(12) United States Patent
Jaeger et al.

(10) Patent No.: US 11,547,796 B2
(45) Date of Patent: Jan. 10, 2023

(54) MEDICAL DEVICE FOR TRANSCUTANEOUSLY INSERTING A CANNULA INTO A BODY TISSUE

(71) Applicant: Roche Diabetes Care, Inc., Indianapolis, IN (US)

(72) Inventors: Joachim Jaeger, Bruchsal (DE); Nadine Exner, Stuttgart (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 16 days.

(21) Appl. No.: 17/145,063

(22) Filed: Jan. 8, 2021

(65) Prior Publication Data
US 2021/0146043 A1 May 20, 2021

Related U.S. Application Data

(63) Continuation of application No. PCT/EP2019/067515, filed on Jul. 1, 2019.

(30) Foreign Application Priority Data

Jul. 9, 2018 (EP) .................................... 18182451

(51) Int. Cl.
*A61M 5/158* (2006.01)

(52) U.S. Cl.
CPC ..... *A61M 5/158* (2013.01); *A61M 2005/1585* (2013.01); *A61M 2005/1586* (2013.01); *A61M 2205/0216* (2013.01)

(58) Field of Classification Search
CPC .......... A61M 5/158; A61M 2005/1585; A61M 2005/1586; A61M 2205/0216;
(Continued)

(56) References Cited

U.S. PATENT DOCUMENTS

| 2007/0088272 A1* | 4/2007 | Jones ................ A61M 25/0637 604/192 |
| 2012/0053522 A1* | 3/2012 | Yodfat ................ A61M 5/1723 604/151 |
| 2012/0232518 A1 | 9/2012 | Yodfat et al. |

FOREIGN PATENT DOCUMENTS

| WO | WO 02/40083 A2 | 5/2002 |
| WO | WO 2005/002649 A1 | 1/2005 |

(Continued)

OTHER PUBLICATIONS

International Search Report and Written Opinion of the International Searching Authority, PCT/EP2019/067515, dated Oct. 1, 2019, 11 pages.

*Primary Examiner* — Bhisma Mehta
*Assistant Examiner* — Phoebe Anne Staton
(74) *Attorney, Agent, or Firm* — Bose McKinney & Evans LLP

(57) ABSTRACT

An inventive medical device for transcutaneously inserting a cannula into body tissue. The device has a cannula with a wall that at least partially encloses a lumen. The device also has a patch for mounting onto skin of a user. The patch has a base and has a reservoir for storing a medical fluid. The patch also has a spring driven inserter. The inserter has a drive that urges the cannula from a storage position within the patch to an inserted position within the body tissue. The inserter also has a lock configured for securing the drive in a fixed position. The lock is fixedly connected to the drive and has a snap closure. Also disclosed is a medication pump that is fluidly connectable to the cannula. A method of transcutaneously using the medical device to transcutaneously insert a cannula into body tissue is also disclosed.

19 Claims, 8 Drawing Sheets

(58) Field of Classification Search
CPC ...... A61M 2005/14268; A61M 5/1454; A61M 5/14248; A61M 5/1413; A61M 5/14244
See application file for complete search history.

(56) References Cited

FOREIGN PATENT DOCUMENTS

| | | | |
|---|---|---|---|
| WO | WO 2011/046950 A1 | 4/2011 | |
| WO | WO 2013/140395 A1 | 9/2013 | |
| WO | WO-2013182321 A1 * | 12/2013 | .......... A61M 5/1415 |
| WO | WO 2017/220681 A1 | 12/2017 | |
| WO | WO 2017/220683 A1 | 12/2017 | |
| WO | WO-2017220681 A1 * | 12/2017 | ......... A61B 17/3415 |

* cited by examiner

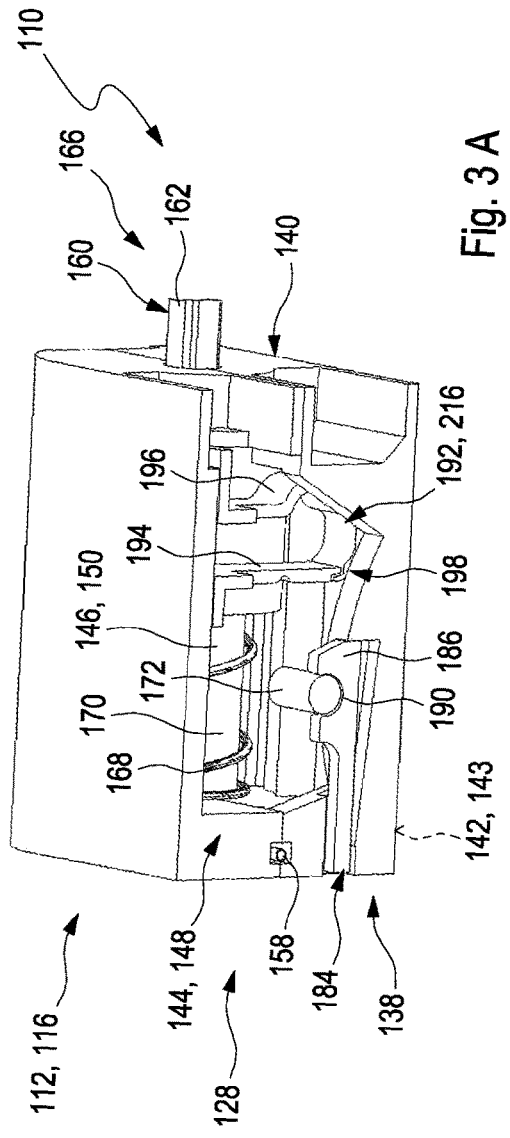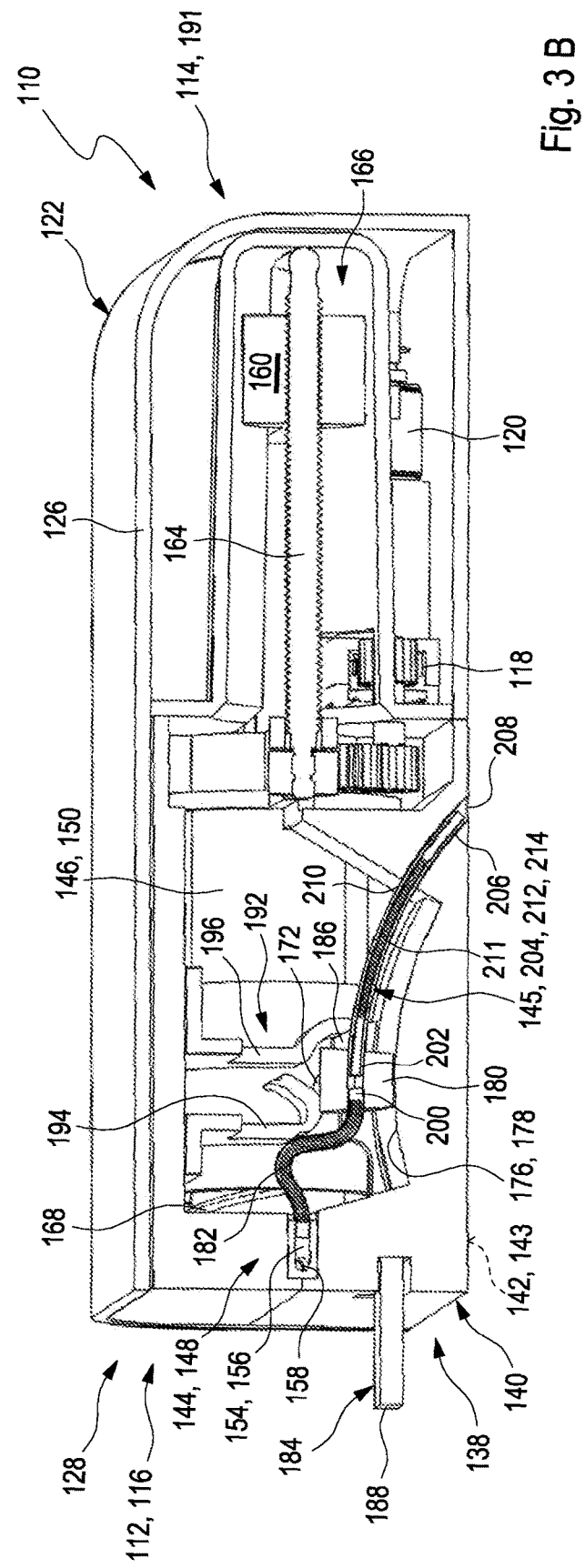

MEDICAL DEVICE FOR TRANSCUTANEOUSLY INSERTING A CANNULA INTO A BODY TISSUE

RELATED APPLICATIONS

This application is a continuation of PCT/EP2019/067515, filed Jul. 1, 2019, which claims priority to EP 18 182 451.7, filed Jul. 9, 2018, the entire disclosures of both of which are hereby incorporated herein by reference.

BACKGROUND

This disclosure relates to a medical device for transcutaneously inserting a cannula into a body tissue, a medication device for delivering at least one medication to a user and a method for transcutaneously inserting a cannula into a body tissue. The method and devices according to this disclosure may mainly be used for delivering insulin to a user. This disclosure may both be applied in the field of home care as well as in the field of professional care, such as in hospitals. Other applications are generally feasible.

Delivering medicine to a user, specifically insulin delivery, plays an important role in the prevention and treatment of diseases, in particular in the treatment of diabetes mellitus. Besides using injection pens or syringes, insulin delivery may specifically be performed by using insulin pumps.

In particular, a user is generally required to wear the insulin pump on his or her body at all times, thus leading to a preferably small and compact construction of the insulin pump and its components. Common pumps for delivering medicine, such as for example insulin, comprise a plurality of medicine reservoirs. As an example, fluid delivery devices are disclosed in WO2011/046950 A1. The fluid delivery device comprises a housing having a fluid reservoir. A needle is in fluid communication with the fluid reservoir in an engaged position and out of fluid communication with the fluid reservoir in armed and storage positions. A proximal end of a biasing member is coupled to the housing and a distal end of the biasing member is configured to deliver a force to the fluid reservoir. A piston member extends through the biasing member and is coupled to the distal end of the biasing member. The piston member is fixed with respect to the housing in a locked position such that the biasing member does not deliver the force to the fluid reservoir and the piston member is moveable with respect to the housing in a released position such that the biasing member delivers the force to the fluid reservoir. Transitioning the needle from the storage position to the armed position transitions the piston from the locked position to the released position.

WO 2005/002649 A1 describes medical devices which are adapted for application to a skin surface of a user and comprise a transcutaneous device which is supplied in a sterile condition. Thus, a medical device is provided, comprising a mounting surface adapted for application to the skin of a subject, a first portion having a first end adapted to penetrate the skin of the subject, and a second portion in fluid communication with the first portion and having a second end. The device further comprises enclosure means being transformable from an initial configuration encapsulating the first and second portions in an initial aseptic state, to a second configuration in which the ends of the first and second portions are allowed to communicate with the exterior through the enclosure means, wherein the enclosure means does not enclose the mounting surface.

WO 2017/220681 A1 describes a medical device for transcutaneously inserting an insertable element into a body tissue is disclosed. The medical device comprises: at least one insertable element, wherein the insertable element comprises at least one in vivo distal end for subcutaneous insertion and at least one ex vivo proximal end; at least one insertion cannula for subcutaneously inserting the insertable element, the insertion cannula having a lumen which fully or partially is enclosed by a wall of the insertion cannula, wherein the insertable element is received in the lumen, wherein the insertion cannula is a pre-bended insertion cannula. The medical device further comprises at least one patch which is configured to be mounted onto a skin of a user. The patch comprises a patch base. The patch comprises an integrated insertion mechanism for driving the insertion cannula from a storage position within the patch into an inserted position within the body tissue on a curved insertion path.

Despite the advantages of state of the art pumps for delivering insulin, several technical challenges remain. Commonly, the cannula is inserted via a separate insertion unit or via electro mechanics which are positioned within a patch. However, due to the external insertion unit, there is an external interface and additional handling steps are required. In case electro mechanics are applied, there is an increased manufacturing effort which leads to increased costs.

SUMMARY

This disclosure teaches a medical device for transcutaneously inserting a cannula into a body tissue, a medication device for delivering at least one medication to a user and a method for transcutaneously inserting a cannula into a body tissue, which at least partially avoid the shortcomings of known devices and methods of this kind and which at least partially address the above-mentioned challenges. Specifically, devices and methods shall be disclosed which allow for easy manufacturing and simple handling processes by a user.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once, typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "cannula," "patch," and "reservoir," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

The terms "patient" and "user" as used herein are broad terms and are to be given their ordinary and customary meaning to a person of ordinary skill in the art and are not to be limited to a special or customized meaning. The terms specifically may refer, without limitation, to a human being or an animal, independent from the fact that the human being or animal, respectively, may be in a healthy condition or may suffer from one or more diseases. As an example, the patient or the user may be a human being or an animal suffering from diabetes. However, additionally or alternatively, the invention may be applied to other types of users or patients or diseases.

The term "body tissue" as used herein is a broad term and is to be given its ordinary and customary meaning to a person of ordinary skill in the art and is not to be limited to a special or customized meaning. The term specifically may refer, without limitation, to a cellular organizational level intermediate between cells and a complete origin. The body tissue may specifically be an ensemble of similar cells from the same origin that together carry out a specific function. Thereby, organs may then be formed by functional grouping together of multiple tissues. As an example for body tissue, interstitial tissue, i.e., connective tissue between cellular elements if a structure, may be named.

In a first aspect of this disclosure, a medical device for transcutaneously inserting a cannula into a body tissue is disclosed. The medical device comprises at least one cannula. The cannula comprises a lumen which is fully or partially enclosed by a wall of the cannula. Further, the medical device comprises at least one patch configured to be mounted onto a skin of a user. The patch comprises at least one patch base. The patch further comprises at least one integrated insertion mechanism for driving the cannula from a storage position within the patch into an inserted position within the body tissue. The patch further comprises at least one reservoir configured for storing at least one therapeutical medical fluid. Further, the integrated insertion mechanism is a spring driven insertion mechanism.

The term "medical device" as used herein is a broad term and is to be given its ordinary and customary meaning to a person of ordinary skill in the art and is not to be limited to a special or customized meaning. The term specifically may refer, without limitation, to an arbitrary device configured for conducting at least one medical procedure. The medical device therefore generally may be an arbitrary device configured for performing at least one therapeutic purpose. The medical device specifically may comprise one component or an assembly of two or more components capable of interacting with each other, such as in order to perform one or more therapeutic purposes, such as in order to perform the medical procedure. The medical device generally may also be or may comprise at least one of a medical system or a medical kit. The medical device generally may be used for delivering at least one medication such as a drug and/or a therapeutic agent to a user. Thus, the medical device may be used as part of one or more medical treatments.

The medical device may specifically be a disposable medical device. The term "disposable" as used herein is a broad term and is to be given its ordinary and customary meaning to a person of ordinary skill in the art and is not to be limited to a special or customized meaning. The term specifically may refer, without limitation, to the property of a component or an element to be disposed of after use. Thus, the disposable element or component may be designed to be irreversibly altered or even destroyed during use, such as by mechanical deformation or by irreversible separation of components of the disposable element. Thus, the disposable element may be configured to be disposed of after use. Thus, this component may be made of at least one material which specially may be low priced and/or easily recyclable. Still, other embodiments are feasible.

The medical device may be provided in a sterile packaging before usage. The term "packaging" may refer to an arbitrary object which is configured for fully or partially enclosing or encasing at least one other component, wherein the at least one other component, as an example, may be a component which requires protection, such as mechanical protection and/or protection against moisture and/or microbial contaminations. The term "sterile" may generally refer to a property of an arbitrary object of being at least to a large extent free from all forms of life and/or other biological agents such as prions, viruses, fungi, bacteria or spore forms. Thus, the sterile object may be treated by at least one sterilization process that one or more of reduces, eliminates or deactivates the forms of life and/or of the other biological agents.

The term "transcutaneous" as used herein is a broad term and is to be given its ordinary and customary meaning to a person of ordinary skill in the art and is not to be limited to a special or customized meaning. The term specifically may refer, without limitation, to a property of an arbitrary element of being adapted to be fully or at least partly arranged through the body tissue of the patient or the user. For this purpose, the element may comprise an insertable portion. In order to further render the element to be usable as a transcutaneous element, the element may fully or partially provide a biocompatible surface, i.e., a surface which, at least during durations of use, does not have any detrimental effects on the user, the patient or the body tissue. Further, the transcutaneous element generally may be dimensioned such that a transcutaneous insertion of the element into the body tissue is feasible, such as by providing a width in a direction perpendicular to an insertion direction of no more than 5 mm, preferably of no more than 2 mm, more preferably of no more than 1.5 mm. Thus, the term "subcutaneous" may generally refer to a property of an arbitrary element of being situated or lying under the skin and within the body tissue of the user or the patient. Specifically, the object may be configured to be introduced under the skin, for example, as an injection.

The term "cannula" as used herein is a broad term and is to be given its ordinary and customary meaning to a person of ordinary skill in the art and is not to be limited to a special or customized meaning. The term specifically may refer, without limitation, to an arbitrary element which may be insertable at least partially into an arbitrary body tissue, particularly in order to deliver or to transfer a further element. Therefore, the cannula may specifically be or may comprise a hollow tube or a hollow needle.

As described above, the cannula has a lumen which is fully or partially enclosed by a wall of the cannula. The term "lumen" as used herein is a broad term and is to be given its ordinary and customary meaning to a person of ordinary skill in the art and is not to be limited to a special or customized meaning. The term specifically may refer, without limitation, to an interior volume of an arbitrary element. The interior volume may specifically be an open interior volume. Thus, the interior volume may not be fully enclosed or surrounded by a wall of the element. Instead, a flow of a fluid medium or an insertion of another object from one end of the element to a further end through the lumen may be feasible.

The term "wall" as used herein is a broad term and is to be given its ordinary and customary meaning to a person of ordinary skill in the art and is not to be limited to a special or customized meaning. The term specifically may refer, without limitation, to an arbitrary structure, specifically a structural material, which is configured to at least partially surround another object or volume thereby defining physical limits of an object. Further, the wall may be configured to protect the volume or the other object at least partially enclosed by the wall.

Specifically, the cannula may be selected from the group consisting of: a closed cannula with the wall circumferentially enclosing the lumen; The term "circumferentially enclosing" may generally refer to a property of an arbitrary object or volume of being fully enclosed by another object in at least two dimensions. Specifically, the lumen of the cannula may be fully enclosed by the cannula in directions perpendicular to a direction of extension of the cannula.

The cannula may be selected from the group consisting of: an insertion cannula for inserting an infusion cannula; an infusion cannula. The term "infusion cannula" as used herein is a broad term and is to be given its ordinary and customary meaning to a person of ordinary skill in the art and is not to be limited to a special or customized meaning. The term specifically may refer, without limitation, to an arbitrary cannula being configured to introduce an infusion, i.e., a liquid substance, specifically a liquid substance comprising a medicine, into the body tissue, for example, directly into a vein of the patient. Therefore, the infusion cannula may be attached to a reservoir comprising the liquid substance, specifically via the ex vivo proximal end of the infusion cannula. The infusion cannula may be part of an infusion kit. The term "infusion kit" may refer to an assembly of components which are required for a conduction of an arbitrary infusion. Thus, besides of the infusion cannula, the infusion kit may further comprise at least one fluid coupling for coupling the infusion kit to at least one medication device, preferably to at least one medication pump.

Alternatively, the cannula may be an insertion cannula for inserting an infusion cannula. The insertion cannula may specifically be an injection needle. The injection needle may be arranged within a lumen of a soft cannula and the injection needle may be removed after insertion of the soft cannula, e.g., the soft cannula, which is configured to stay at least partially within the body tissue and to stay within the body tissue during the useful lifetime of the medical device. The term "soft cannula" may refer to an arbitrary cannula which is at least partially made of at least one soft, e.g., elastic material. The elastic material may specifically comprise at least one elastic material. Thus, the soft cannula may be or may comprise a flexible tube. Meanwhile, the injection needle may stay outside of the body tissue but may be incorporated within the medical device. Specifically, the injection needle may be protectively enclosed by the medical device such that the injection needle may not be a source of risk to the user or the patient. Thus, the user or the patient may have the injection needle protectively enclosed by the medical device, specifically by a housing of the medical device, attached to the body tissue via medical device. Thus, the injection needle and the soft cannula may be configured to be removed from the body of the patient at the same time after the useful expiration time of the medical device is expired.

The cannula may at least partially be made of at least one biocompatible material, i.e., a surface which, at least during durations of use, does not have any detrimental effects on the user, the patient or the body tissue. The cannula, specifically the infusion cannula, may be at least partially made of steel, specifically stainless steel. The steel, specifically the stainless steel may be biocompatible. Further, by applying the steel, specifically the stainless steel, a rigid infusion cannula may be provided. However, other materials may be feasible, such as a plastic material.

The cannula may be a pre-bended cannula. The term "pre-bended" as used herein is a broad term and is to be given its ordinary and customary meaning to a person of ordinary skill in the art and is not to be limited to a special or customized meaning. The term specifically may refer, without limitation, to a geometrical property of an element which, at least in absence of external forces, is an at least partially non-straight shape. Thus, the insertion cannula, at least in absence of external forces, may be at least partially non-straight. Thus, the cannula specifically may fully or partially be embodied as having a non-straight saying, specifically fully or partially be embodied as having a curved shape. Specifically, the cannula may fully or partially be embodied as having the shape of a segment of a circle. Thus, specifically, the cannula may be pre-bended in such a way that it fully or partially has the shape of a segment of a circle. More specifically, as an example, the pre-bended cannula may be a steel cannula, specifically a stainless steel cannula, being pre-bended in such a way that it is fully or partially curved, specifically having the shape of a segment of a circle.

The cannula may comprise at least one curvature. Thereby, parts of the cannula such as one end of the cannula may be arranged in an angle relative to the major axis. Specifically, the cannula may have an angle of 30° to 60°, preferably of 40° to 45°, more preferably of 45°, to the major axis. Specifically, the second shape configuration may correspond to an arch form of the cannula. The arch form may specifically refer to a state of the cannula, wherein the cannula may be curved such that one part of the cannula, specifically one end of the cannula, more specifically one end of the cannula comprising the in vivo distal end of the insertable element, sticks out from the major axis. Thereby, the curvature may preferably be, at least to a large extent, free from bends.

The infusion cannula may be configured to be removed from the body tissue subsequent to an expiration of a useful lifetime of the medical device. The term "useful lifetime" may refer to a period of time during which an arbitrary device may be applied in an intended manner. Specifically, the medical device may be configured to stay mounted onto the skin of the patient or the user for several days such as for two to four days. During this period of time, the medical device may be configured to transfer an infusion into the body tissue as will further be described below. Further, during this period of time, the cannula may stay within the body tissue.

The term "patch" as used herein is a broad term and is to be given its ordinary and customary meaning to a person of ordinary skill in the art and is not to be limited to a special or customized meaning. The term specifically may refer, without limitation, to a device which is attachable to a skin or a skin site of a user or a patient. Thus, the patch may comprise at least one attachment component which is capable of connecting the body mount to the skin, such as at least one adhesive surface and/or at least one adhesive strip or plaster. Thus, the term "mounting" specifically may refer, without limitation, to an arbitrary process of fixing or attaching an element to an object. The attachment may be a permanent attachment, e.g., the element and the object may have a permanent connection to each other which may not be disconnected when the unit of the element and the object is bent or when a mechanical stress is applied to the element and/or to the object.

As outlined above, the patch comprises the patch base. As further used herein, the term "base" refers to an arbitrary support of an object on which further components of the object rest. Thereby, the base may have a supporting surface serving bearing area for the further components. Specifically, the patch base may be a flat element. The patch base may comprise a bottom surface facing the body tissue of the user or the patient. The bottom surface may be the adhesive surface as described above. Further, the patch base may comprise an upper surface. The upper surface may be configured as bearing surface and may be configured to serve as a host for further components of the medical device. Therefore, the patch may also be referred to a body mount. The patch base may comprise at least one passage opening. The cannula may be movable from the patch into the body tissue through the passage opening. A shape of the passage opening may correspond to a shape of the cannula.

The term "reservoir" as used herein is a broad term and is to be given its ordinary and customary meaning to a person of ordinary skill in the art and is not to be limited to a special or customized meaning. The term specifically may refer, without limitation, to a hollow element or container which may fully or partially be fillable with a fluid such as with a drug and/or a therapeutic agent. Specifically, the reservoir may be fillable with insulin. The reservoir may be removably placeable within the medical device. Specifically, the insertion cannula may be the infusion cannula as described above and the reservoir may be configured for releasing the therapeutical medical fluid via the cannula. The reservoir may comprise at least one cartridge or vial. The vial may have a cylindrical shape. The reservoir may be a vial, specifically a rigid vial.

The medical device may further comprise at least one further reservoir configured for storing and releasing at least one further therapeutical medical fluid. The reservoir and the further reservoir may be arranged next to each other. Thus, the reservoir and the further reservoir may be arranged in a space saving manner. The medical device may further comprise at least one mixing device. The mixing device may comprise at least one static mixer. The mixing device may be configured for mixing the therapeutical medical fluid of the reservoir and the further therapeutical medical fluid of the further reservoir such that a mixture is formed before the mixture is applied to the user via the cannula.

The medical device may further comprise at least one piston, specifically at least one piston rod. The piston may be configured to displace the therapeutical medical fluid of the reservoir. The term "piston" as used herein is a broad term and is to be given its ordinary and customary meaning to a person of ordinary skill in the art and is not to be limited to a special or customized meaning. The term specifically may refer, without limitation, to an arbitrary moving component that is contained by a cylinder and is made, at least to a large extent, gas-tight and/or watertight by piston rings. In a pump, the piston may be configured to transfer a force from a crankshaft to a cylinder for the purpose of compressing or ejecting a fluid in the cylinder. The term "displacement" as used herein is a broad term and is to be given its ordinary and customary meaning to a person of ordinary skill in the art and is not to be limited to a special or customized meaning. The term specifically may refer, without limitation, to a process of reducing a free volume of a defined interior space. Thus, by reducing the free volume, a part of a fluid which is received within the defined interior space may leave the interior space, e.g., the fluid may be released from the interior volume.

The medical device may further comprise at least one drive spindle. The drive spindle may be operably connectable to at least one medication pump. The term "drive spindle" as used herein is a broad term and is to be given its ordinary and customary meaning to a person of ordinary skill in the art and is not to be limited to a special or customized meaning. The term specifically may refer, without limitation, to an arbitrary rotatable axis which is configured to urge another element in a desired direction preferably by pushing or pulling the other element. Specifically, the drive spindle may be configured for pushing or pulling the other element in a linear manner. As described above, the medical device may comprise the at least one piston. The medication pump may be configured to move the piston via the drive spindle. Thus, by rotating the drive spindle, the piston may displace the therapeutical fluid of the reservoir.

The term "insertion mechanism" (also referred to as an "inserter") may generally refer to an assembly of components which are configured to interact with each other with the purpose of inserting an element at least partially into another object. Therefore, the insertion mechanism may be configured such that a movement of the element in a direction of insertion, i.e., toward a surface of the other object, is introduced. The insertion mechanism may be an integrated insertion mechanism. The term "integrated insertion mechanism" may refer to an assembly of the components which are configured to interact with each other with the purpose of inserting the element at least partially into another object, wherein the assembly of the components is provided as one unit, as a whole and/or as an "all-in-one" system. Thus, the user may find the medical device comprising a fully assembled insertion mechanism without the need to add other components to the medical device or the need to apply a further device in addition to the medical device for the purpose of inserting the cannula into the body tissue. Further, optionally, the integrated insertion mechanism may be also configured for subsequently driving the cannula back from the inserted position into the storage position. However, the medical device may also be configured for removing the medical device from the body tissue while the cannula is in the inserted position as further described below in more detail.

The term "storage position" as used herein is a broad term and is to be given its ordinary and customary meaning to a person of ordinary skill in the art and is not to be limited to a special or customized meaning. The term specifically may refer, without limitation, to a position of the cannula within the patch, in which the cannula does not protrude into the body tissue. Specifically, the cannula may be fully or partially surrounded by the patch. The term "inserted position" as used herein is a broad term and is to be given its ordinary and customary meaning to a person of ordinary skill in the art and is not to be limited to a special or customized meaning. The term specifically may refer, without limitation, to a position of the cannula in which the cannula fully or partially protrudes from the patch, such as by fully or partially protruding into the body tissue, which preferably a proximal end of the cannula is fully or partially held by the patch or connected to the patch. In the storage position and in the inserted position, the cannula may have the same shape or may have a different shape. For example, the cannula may have the same bending radius or the same shape in the storage position.

The integrated insertion mechanism may be configured for driving the cannula into the body tissue of the user or the patient on a curved path. The term "on a curved path" as used herein is a broad term and is to be given its ordinary and customary meaning to a person of ordinary skill in the art and is not to be limited to a special or customized meaning. The term specifically may refer, without limitation, to the fact that a tip of the cannula, during movement from the storage position into the inserted position, follows a path which is at least partially non-straight. Specifically, the path may at least partially have the shape of a segment of a circle.

The term "spring driven insertion mechanism" (also referred to as "spring driven inserter") as used herein is a broad term and is to be given its ordinary and customary meaning to a person of ordinary skill in the art and is not to be limited to a special or customized meaning. The term specifically may refer, without limitation, to an arbitrary insertion mechanism, wherein an interaction of an assembly of components for the purpose of inserting an element at least partially into another object is driven or triggered by a spring element. Thus, a force may be created by a spring, specifically by a force which is set free when a tensioned spring is released from a tensioned position. As a consequence, by releasing the spring from the tensioned position, the cannula may be urged in a direction of insertion, preferably by pushing or pulling the cannula.

The integrated insertion mechanism (also referred to as "integrated inserter"), specifically the spring driven insertion mechanism, may be a manual insertion mechanism. The term "manual insertion mechanism" or "manual inserter" as used herein is a broad term and is to be given its ordinary and customary meaning to a person of ordinary skill in the art and is not to be limited to a special or customized meaning. The term specifically may refer, without limitation, to an arbitrary insertion mechanism, wherein the insertion mechanism is triggered or conducted just by applying mechanical forces. The mechanical forces, e.g., a tensioning of the spring element as described above or as will further be described below in more detail, may be created by a manual procedure of the user or the patient, as will further be described below in more detail. Thus, the integrated insertion mechanism may be triggerable without a need of an electrical energy source. The medical device, specifically the patch base, may be connectable to at least one external element interacting with the cannula. The integrated insertion mechanism may be configured to be driven by a force established when connecting the external element to the medical device.

The integrated insertion mechanism may comprise at least one drive unit (or "drive") configured for urging the cannula in a direction of insertion, preferably by pushing the cannula. The term "drive unit" (also referred to as a "drive") as used herein is a broad term and is to be given its ordinary and customary meaning to a person of ordinary skill in the art and is not to be limited to a special or customized meaning. The term specifically may refer, without limitation, to an element or an assembly of elements which are configured to interact with each other in order to create a force leading a movement, specifically a pre-determined movement, of another element. Specifically, the drive unit may be configured to urge the cannula in a direction of insertion, preferably by pushing or pulling the cannula. Specifically, the drive unit may be configured for moving in a direction of extension of the reservoir. Thus, the drive unit may at least partially surround the reservoir and may be configured to move along the reservoir.

The integrated insertion mechanism may be a sliding mechanism, preferably a linear sliding mechanism. The term "sliding mechanism" (also referred to as a "sliding inserter") as used herein is a broad term and is to be given its ordinary and customary meaning to a person of ordinary skill in the art and is not to be limited to a special or customized meaning. The term specifically may refer, without limitation, to an arbitrary mechanism which is based on a linear sliding movement of two or more components relative to each other. Thereby, the term "sliding movement" may refer to a movement along a continuous connection with another element, specifically with a surface, more specifically of a smooth surface, of the other element. Specifically, the linear sliding mechanism may comprise one or more interacting sliding elements, such as one or more guide rails or the like. Further, the term "linear sliding movement" may generally refer to a movement along a straight line, e.g., within two dimensions.

The integrated insertion mechanism may further comprise at least one spring element. The term "spring element" (also referred to as a "spring") as used herein is a broad term and is to be given its ordinary and customary meaning to a person of ordinary skill in the art and is not to be limited to a special or customized meaning. The term specifically may refer, without limitation, to an arbitrary elastic object which is used to store mechanical energy. In case an object may be coupled to the spring element, the spring element may be configured to be tensioned when the object is moved. Thereby, the spring element may be configured to move the object back to its original position when the spring element is relaxed. Specifically, the spring element may be configured to be tensioned before insertion of the cannula into the body tissue. Further, the spring element may be configured to support an insertion of the cannula into the body tissue. The spring element may, for example, be a spiral spring element and/or a compression spring element.

Specifically, the spring element may be tensible parallel to a direction of insertion, i.e., extended and contracted in a direction parallel to the direction of insertion. The drive unit may be configured to compress the spring element as will further be described below in more detail. Thus, the spring element may be configured to relax in the direction of insertion, thereby pushing the cannula in the direction of insertion. Specifically, the reservoir may be at least partially received within the spring element. Further, the cannula may be at least partially received within the spring element. Thus, the components of the medical device may be arranged in a space saving manner and a construction size of the medical device may be reduced. The spring element may be configured to prevent at least to a large extent, a withdrawing of the cannula from the body tissue after insertion. Thus, in the inserted position, the cannula may be at least partially inserted into the body tissue. The spring element may be existent in a relaxed state, thereby applying a force on the cannula in a direction of insertion, specifically on an ex vivo end of the cannula.

Further, the medical device may comprise a decoupling of a movement of the cannula. The spring element may be configured to be tensioned parallel to a direction of insertion. Thus, the cannula may be flexible in the direction of insertion.

The integrated insertion mechanism may further comprise at least one interlocking element configured for securing the drive unit in fixed position. The term "interlocking element" (also referred to as a "lock") as used herein is a broad term and is to be given its ordinary and customary meaning to a person of ordinary skill in the art and is not to be limited to a special or customized meaning. The term specifically may refer, without limitation, to hold or secure an object in a certain position in order to prevent an undesired movement or separation from another element, specifically through an application of an inward pressure. The interlocking element may be fixedly connected to the drive unit.

The interlocking element may comprise at least one first interlocking element component and at least one second interlocking element component, wherein the first interlocking element component and the second interlocking element component are at least partially made of an elastic material, wherein the first interlocking element component and the second interlocking element component are configured to form a mechanical connection, specifically a form-fit connection. The form-fit connection may be a releasable form-fit connection. The interlocking element may have a snap closure. The term "snap closure" may refer to an arbitrary closure which engages via a snapping or clip mechanism. The clicking mechanism may be a one-way clip mechanism.

The medical device may further comprise at least one elongate element. The elongate element may extend in a direction transverse, particularly perpendicular to a direction of extension of the cannula. The cannula, specifically at least one end of the cannula, may be fixedly received within a receptacle of the elongate element. The patch base may comprise a sliding guide receptacle, preferably a linear sliding guide receptacle. The linear sliding guide receptacle may be configured for receiving a protrusion of the elongate element at least partially. The receptacle may specifically be part of the protrusion. The protrusion may be configured to slide within the linear sliding guide receptacle. The linear sliding guide receptacle may extend in a direction transverse, particularly perpendicular to a direction of extension of the cannula. The reservoir may be connectable to the cannula via at least one fluid channel. The fluid channel may, for example, be a flexible tube. One end of the fluid channel may be received in the protrusion of the elongate element. Further, the ex vivo proximal end of the cannula may also be at least partially received within the protrusion of the elongate element. Thus, the protrusion may be configured to establish a fluid connection between the fluid channel, e.g., the reservoir, and the cannula.

The interlocking element may be configured to enclose the elongate element. Thus, before insertion, when the cannula is in the storage position, the interlocking element may be moved in a direction reverse the direction of insertion. Thus, the interlocking element may be opened, thereby enclosing the elongate element and establishing a fixed connection with the elongate element.

The integrated insertion mechanism may further comprise at least one release button. The release button may be an elongate element with a first end and a second end. The first end may have a receptacle. The receptacle may have a shape which corresponds to a shape of the elongate element. For example, the elongate element may be a cylinder having a round cross-section and the receptacle may have a round shape correspondingly. A second end of the release button may be located outside of the patch. Thus, the second end may be accessible for the user or the patient. The release button may be configured for holding the elongate element in a predetermined position and for subsequently releasing the elongate element. The release button may be configured to be pressed, thereby triggering the integrated insertion mechanism. Thus, the integrated insertion mechanism may be triggerable manually. However, other embodiments may be feasible. For example, the integrated insertion mechanism may be triggered as soon as the medical device and the external element are assembled. Thereby, the medical device may be arranged and fixedly applied on the skin site of the user prior to the assembly of the medical device and the external element. However, also other embodiments may be feasible. The integrated insertion mechanism may also be a button-free integrated insertion mechanism. For example, the integrated insertion mechanism may be triggered as soon as the external element is connected to the medical device.

In a further aspect of this disclosure, a medication device for delivering at least one therapeutical medical fluid to a user is disclosed. The medication device comprises at least one first part. The first part comprises at least one medical device as described above or as will be described in further detail below. Further, the medication device comprises at least one second part. The second part comprises at least one medication pump fluidically connectable to the cannula. Further, the second part comprises at least one electronics unit.

The medication device comprises at least one medical device as described above or as will further be described below.

The term "medication device" as used herein is a broad term and is to be given its ordinary and customary meaning to a person of ordinary skill in the art and is not to be limited to a special or customized meaning. The term specifically may refer, without limitation, to an arbitrary device which is configured to administer or deliver a drug and/or a therapeutic agent via a specific route of administration. Such devices are commonly used as part of one or more medical treatments. Specifically, the term "medication device" may refer to a device for administering insulin by using at least one pump.

The terms "first" and "second," as generally used herein for denoting components or elements, may be considered as nomenclature only, without numbering or ranking the named elements, without specifying an order and without excluding a possibility that several kinds of first parts and second parts may be present. Further, additional parts such as one or more third parts or elements may be present. The term "part" may refer to an arbitrary component of an object. The component may be configured for interacting with a further component of the object. Specifically, the first part and the second part of the medication device may be capable of interacting with each other, such as in order to perform one or more therapeutic purposes, such as in order to perform the medical procedure as outlined above. The first part may be a disposable component and the second part may be a reusable component. The second part and/or the first part may be a watertight component. Specifically, the medication device may be a watertight medication device. For this purpose, the second part may have one or more sealing elements which may be configured to be pressed against at least one surface of the first component. Thus, an interior formed by the first part and the second part may be enclosed in a watertight manner.

The term "medication pump" as used herein is a broad term and is to be given its ordinary and customary meaning to a person of ordinary skill in the art and is not to be limited to a special or customized meaning. The term specifically may refer, without limitation, to an arbitrary pump which is configured to move a drug and/or a therapeutic agent by mechanical action. Specifically, the medication pump may be an infusion pump which is configured to infuse an arbitrary medication into a patient's circulatory system. Generally, the infusion pump may be configured to be applied intravenously or subcutaneously. However, other applications are feasible. The medication pump may be a positive displacement pump. The positive displacement pump may be configured to move at least one piston of the medical device in a direction of extension of the reservoir, specifically via at least one drive spindle of the medical device.

The terms "fluidically coupled" or "fluidically connectable" or "fluidly coupled" may generally refer to a property of two or more elements such that an arbitrary fluid may be transferable between the two or more elements. The medication pump may specifically be an insulin pump. The term "insulin pump" as used herein is a broad term and is to be given its ordinary and customary meaning to a person of ordinary skill in the art and is not to be limited to a special or customized meaning. The term specifically may refer, without limitation, to a device for administering insulin by using at least one pump. The term "fluidically connectable" may thus also be referred to as "operably connectable," as far as a fluidic operation is concerned.

The term "electronics unit" (or merely "electronics") as used herein is a broad term and is to be given its ordinary and customary meaning to a person of ordinary skill in the art and is not to be limited to a special or customized meaning. The term specifically may refer, without limitation, to an arbitrary device having at least one electronic component. Specifically, the electronics unit may comprise at least one electronic component for one or more of performing a measurement with the sensor, performing a voltage measurement, performing a current measurement, recording sensor signals, storing measurement signals or measurement data, transmitting sensor signals or measurement data to another device. The electronics unit may specifically be embodied as a transmitter or may comprise a transmitter, for transmitting data. Other embodiments of the electronic components are feasible. The electronics unit may comprise at least one interconnect device, preferably a printed circuit board, more preferably a flexible printed circuit board. The electronics unit may specifically be configured for controlling and operating the medication pump. Further, the second part may comprise at least one energy storage device. The energy storage device may be part of the electronics unit. The energy storage device may be selected from the group consisting of: a battery, a rechargeable battery, an accumulator. Also other embodiments are feasible.

The first part and the second part may be configured to establish at least one mechanical connection, selected from the group consisting of: a form-fit connection, a press-fit connection. As used herein, the term "mechanical connection" generally refers to a connection of two or more components by mechanical holding forces. As an example, the mechanical connection may be or may comprise at least one of a form-fit or a force-fit connection. As further used herein, the term "releasable," in the context of the mechanical connection, generally refers to the fact that the mechanical connection may be brought from a disconnected state, also referred to as a non-mated state, into a connected state, also referred to as a mated state, and back into the disconnected state. Thus, the mechanical connection may be closed and released at will. Specifically, the mechanical connection may be releasable without using any tools, simply by manual action. As an example, for opening a connection between the first part and the second part, forces of no more than 50 N, such as of no more than 20 N, such as of no more than 10 N, may be required, which may be applied by one hand or even the fingers or fingertips of the user.

Specifically, the first part and the second part may be connectable via at least one linear sliding mechanism. The first part may comprise at lease one linear sliding receptacle and the second part may comprise at least one linear sliding guide rail or vice versa. The linear sliding receptacle and the linear sliding guide rails in conjunction may form a linear sliding connector configured for establishing a releasable mechanical connection between the first part and the second part. As further used herein, the terms "linear sliding receptacle" and "linear sliding guide rail" may refer to elements which are complementary to each other and which are configured to interact with each other in order to realize the linear sliding mechanism. For example, the linear sliding guide rail may be formed as a protrusion of the first part and the linear sliding receptacle may be the second part or vice versa. However, other embodiments may be feasible. The linear sliding guide rail and the linear sliding receptacle may be shaped complementary to each other. For example, the linear sliding receptacle and the linear guide rail may have an elongate shape and may extend along a longitudinal axis of the first part and/or of the second part. The linear sliding receptacle and the linear sliding guide rail in conjunction may form a linear sliding connector configured for establishing a releasable mechanical connection between the electronics unit and the patch. The term "linear sliding connector," also referred to as a linear sliding connection, may generally refer to an arbitrary connector or connection between two linear sliding contours. Therein, generally, one or both of the linear sliding contours involved may comprise at least one protrusion and, in a complementary fashion, the other one of the linear sliding contours may comprise at least one linear sliding groove or linear sliding slot in which the protrusion may be guided in order to form the linear sliding connection or linear sliding connector.

By connecting the first part and the second part, the interlocking element may be moved in a direction reverse the direction of insertion. Thus, the interlocking element may be opened, thereby enclosing the elongate element and establishing a fixed connection with the elongate element.

In a further aspect of this disclosure, a method for transcutaneously inserting a cannula into a body tissue is disclosed. The method comprises the method steps as given in the independent claims and as listed as follows. The method steps may be performed in the given order. However, other orders of the method steps are feasible. Further, one or more of the method steps may be performed in parallel and/or in a timely overlapping fashion. Further, one or more of the method steps may be performed repeatedly. Further, additional method steps may be present which are not listed.

The method comprises the following steps:
a) providing a medication device as described above or as will be described in further detail below;
b) placing the first part onto the skin of the user;
c) assembling the first part and the second part such that the first part and the second part establish at least one connection selected from the group consisting of: a form-fit connection, a press-fit connection; and
d) triggering the integrated insertion mechanism, thereby driving the cannula from the storage position within the patch into the inserted position within the body tissue.

Step b) may be performed before conducting step c). Alternatively, step b) may be performed after conducting step c).

The proposed medical device, the analyte measurement device, the medication device and the proposed method for transcutaneously inserting an insertable element into a body tissue provide many advantages over known devices and methods.

Commonly, the infusion cannula may be inserted via a separate insertion unit or via electro mechanics which are positioned within a patch. However, due to the external insertion unit, there is an external interface and additional handling steps are required. In case electro mechanics are applied, there is an increased manufacturing effort which leads to increased costs.

On the contrary, the medical device, the medication device and the method according to this disclosure allow for easy manufacturing and simple handling processes by a user. Further, a necessity of utilizing a separate insertion unit may be avoided. Thus, additional mounting elements as well as an additional manufacturing process may be omitted.

Energy for inserting the cannula may be afforded via an insertion mechanism which is integrated within the patch. An electrical drive may not be necessary. The cannula may have an arch shape and may be arranged within the patch in a space saving manner. Further, the cannula may be a guided cannula and may only require a small opening within the patch base. Thus, an insertion of the cannula may be feasible with an only low deformation of the tissue of the user or the patient.

Further, the spring elements may be arranged within the patch in a space saving manner. Specifically, the reservoir may be arranged within an interior of the spring element or the cannula may be arranged within the interior of the spring element.

Further, after insertion, the cannula may be arranged centrally below the patch. Thus, the cannula may be able to move elastically during application of the medical device. As a consequence, a wearing comfort may be increased.

A handling effort of the user or the patient may be decreased as the second part, comprising the medication pump and the electronics unit, may serve as a slider for tensioning the spring element.

Through the watertight design of the medication device, the medication device does not need to be removed from the skin site of the user or the patient for doing the shower, taking a bath or swimming. The second part may be reusable and the battery may be exchanged by the user or the patient himself. Alternatively, the second part may have an accumulator and the second part may have a covering for a charging contact. Further, an inductive charging may be provided.

By applying a plurality of reservoirs such as by applying two of the reservoirs, the medical device may be designable in a flat manner. Further, by applying a plurality of reservoirs more than one kind of fluid may be applied.

Summarizing and without excluding further possible embodiments, the following embodiments may be envisaged:

Embodiment 1: A medical device for transcutaneously inserting a cannula into a body tissue, wherein the medical device comprises:
at least one cannula, wherein the cannula comprises a lumen which is fully or partially enclosed by a wall of the cannula;
at least one patch configured to be mounted onto a skin of a user, wherein the patch comprises at least one patch base, wherein the patch further comprises at least one integrated insertion mechanism for driving the insertion cannula from a storage position within the patch into an inserted position within the body tissue; and
wherein the patch further comprises at least one reservoir configured for storing at least one therapeutical medical fluid and wherein the integrated insertion mechanism is a spring driven insertion mechanism.

Embodiment 2: The medical device according to the preceding embodiment, wherein the medical device is a disposable medical device.

Embodiment 3: The medical device according to any one of the preceding embodiments, wherein the integrated insertion mechanism is a sliding mechanism, preferably a linear sliding mechanism.

Embodiment 4: The medical device according to any one of the preceding embodiments, wherein the integrated insertion mechanism comprises at least one drive unit configured for urging the cannula in a direction of insertion, preferably by pushing the cannula.

Embodiment 5: The medical device according to the preceding embodiment, wherein the drive unit is configured for moving in a direction of extension of the reservoir.

Embodiment 6: The medical device according to any one of the two preceding embodiments, wherein the drive unit at least partially surrounds the reservoir and is configured to move along the reservoir.

Embodiment 7: The medical device according to any one of the three preceding embodiments, wherein the medical device, specifically the patch base, is connectable to at least one external element, wherein the integrated insertion mechanism is configured to be driven by a force established when connecting the external element to the medical device.

Embodiment 8: The medical device according to any one of the four preceding embodiments wherein the integrated insertion mechanism further comprises at least one spring element.

Embodiment 9: The medical device according to the preceding embodiment, wherein the spring is tensible parallel to a direction of insertion.

Embodiment 10: The medical device according to the preceding embodiment, wherein the drive unit is configured to compress the spring element.

Embodiment 11: The medical device according to any one of the two preceding embodiments, wherein the reservoir is at least partially received within the spring element.

Embodiment 12: The medical device according to any one of the three preceding embodiments, wherein the cannula is at least partially received within the spring element.

Embodiment 13: The medical device according to any one of the four preceding embodiments, wherein the spring element is configured to push the cannula in a direction of insertion.

Embodiment 14: The medical device according to any one of the five preceding embodiments, wherein the spring element is configured to prevent at least to a large extent, a withdrawing of the cannula from the body tissue after insertion.

Embodiment 15: The medical device according to any one of the ten preceding embodiments, wherein the integrated insertion mechanism further comprises at least one interlocking element configured for securing the drive unit in fixed position.

Embodiment 16: The medical device according to the preceding embodiment, wherein the interlocking element is fixedly connected to the drive unit.

Embodiment 17: The medical device according to any one of the two preceding embodiments, wherein the interlocking element has a snap closure.

Embodiment 18: The medical device according to the preceding embodiment, wherein the interlocking element comprises at least one first interlocking element component and at least one second interlocking element component, wherein the first interlocking element component and the second interlocking element component are at least partially made of an elastic material, wherein the first interlocking element component and the second interlocking element component are configured to from a mechanical connection, specifically a form-fit connection.

Embodiment 19: The medical device according to the preceding embodiment, wherein the form-fit connection is a releasable form-fit connection.

Embodiment 20: The medical device according to any one of the five preceding embodiments, wherein the medical device further comprises at least one elongate element having at least one protrusion, wherein the cannula, specifically at least one end of the cannula, is fixedly received within a receptacle of the protrusion, wherein the interlocking element is configured to enclose the elongate element.

Embodiment 21: The medical device according to the preceding embodiment, wherein the integrated insertion mechanism further comprises at least one release button, wherein the release button is configured for holding the elongate element in a predetermined position and for subsequently releasing the elongate element.

Embodiment 22: The medical device according to any one of the two preceding embodiments, wherein the patch base comprises a sliding guide rail, preferably a linear sliding guide rail, wherein the linear sliding guide rail is configured for receiving the protrusion at least partially, wherein the protrusion is configured to slide within the linear sliding guide rail.

Embodiment 23: The medical device according to any one of the three preceding embodiments, wherein the release button is configured to be pressed, thereby triggering the integrated insertion mechanism.

Embodiment 24: The medical device according to any one of the nine preceding embodiments, wherein the interlocking element has a clip mechanism, specifically a one-way clip mechanism.

Embodiment 25: The medical device according to any one of the preceding embodiments, wherein the integrated insertion mechanism is triggerable manually.

Embodiment 26: The medical device according to any one of the preceding embodiments, wherein the medical device further comprises at least one piston, specifically at least one piston rod, wherein the piston is configured to displace the therapeutical medical fluid of the reservoir.

Embodiment 27: The medical device according to the preceding embodiment, wherein the medical device further comprises at least one drive spindle, wherein the drive spindle is operably connectable to at least one medication pump; wherein the medication is configured to move the piston via the drive spindle.

Embodiment 28: The medical device according to any one of the preceding embodiments, wherein the reservoir is connectable to the cannula via at least one fluid channel.

Embodiment 29: The medical device according to the preceding embodiment, wherein the fluid channel is a flexible tube.

Embodiment 30: The medical device according to any one of the preceding embodiments, wherein the reservoir is a vial, specifically a rigid vial.

Embodiment 31: The medical device according to the preceding embodiment, wherein the vial has a cylindrical shape.

Embodiment 32: The medical device according to any one of the preceding embodiments, wherein the cannula is at least partially made of at least one material selected from the group consisting of: steel, specifically stainless steel; a plastic material.

Embodiment 33: The medical device according to any one of the preceding embodiments, wherein the cannula is a pre-bended cannula.

Embodiment 34: The medical device according to any one of the preceding embodiments, wherein the cannula is an infusion cannula, wherein the reservoir is configured for releasing the therapeutical medical fluid via the cannula.

Embodiment 35: The medical device according to the preceding embodiment, wherein the cannula is pre-bended in such a way that the cannula at least partially has the shape of a segment of a circle.

Embodiment 36: The medical device according to any one of the preceding embodiments, wherein the cannula is at least partially made of at least one biocompatible material.

Embodiment 37: The medical device according to any one of the preceding embodiments, wherein the integrated insertion mechanism comprises at least one element configured to prevent at least to a large extent a withdrawing of the cannula from the body tissue after insertion.

Embodiment 38: The medical device according to any one of the preceding embodiments, wherein the integrated insertion mechanism is configured for driving the cannula from a storage position within the patch into an inserted position within the body tissue on a curved insertion path.

Embodiment 39: The medical device according to the preceding embodiment, wherein the insertion path is at least partially shaped as a segment of a circle.

Embodiment 40: The medical device according to any one of the preceding embodiments, wherein the patch base comprises at least one passage opening, wherein the cannula is movable from the patch into the body tissue through the passage opening.

Embodiment 41: The medical device according to the preceding embodiment, wherein a shape of the passage opening corresponds to a shape of the cannula.

Embodiment 42: The medical device according to any one of the preceding embodiments, wherein the medical device further comprises at least one further reservoir configured for storing and releasing at least one further therapeutical medical fluid.

Embodiment 43: The medical device according to the preceding embodiment, wherein the reservoir and the further reservoir are arranged next to each other.

Embodiment 44: The medical device according to any one of the two preceding embodiments, wherein the medical device further comprises at least one mixing device, wherein the mixing device is configured for mixing the therapeutical medical fluid of the reservoir and the further therapeutical medical fluid of the further reservoir such that a mixture is formed before the mixture is applied to the user via the cannula.

Embodiment 45: The medical device according to any one of the three preceding embodiments, wherein the mixing device comprises at least one static mixer.

Embodiment 46: The medical device according to any one of the preceding embodiments, wherein the cannula is at least partially connected to the patch base and/or placed inside the patch base.

Embodiment 47: A medication device for delivering at least one therapeutical medical fluid to a user, wherein the medication device comprises:
  at least one first part, wherein the first part comprises at least one medical device according to any one of the preceding embodiments referring to a medical device; and
  at least one second part, wherein the second part comprises at least one medication pump fluidically connectable to the cannula, wherein the second part further comprises at least one electronics unit.

Embodiment 48: The medication device according to the preceding embodiment, wherein the second part, specifically the electronics unit, has at least one energy supply component, specifically a battery and/or an accumulator.

Embodiment 49: The medication device according to the preceding embodiment, wherein the first part is a disposable component and wherein the second part is a reusable component.

Embodiment 50: The medication device according to any one of the preceding embodiments referring to a medication device, wherein the second part further comprises at least one energy storage device.

Embodiment 51: The medication device according to the preceding embodiment, wherein the energy storage device is selected from the group consisting of: a battery, a rechargeable battery.

Embodiment 52: The medication device according to any one of the preceding embodiments referring to a medication device, wherein the first part and/or the second part is a watertight component.

Embodiment 53: The medication device according to any one of the preceding embodiments referring to a medication device, wherein the medication pump is a positive displacement pump.

Embodiment 54: The medication device according to the preceding embodiment, wherein the positive displacement pump is configured to move at least one piston of the medical device in a direction of extension of the reservoir, specifically via at least one drive spindle of the medical device.

Embodiment 55: The medication device according to any one of the preceding embodiments referring to a medication device, wherein the first part and the second part are configured to establish at least one connection, selected from the group consisting of: a form-fit connection, a press-fit connection.

Embodiment 56: The medication device according to the preceding embodiment, wherein the first part and the second part are connectable via at least one linear sliding mechanism—wherein the first part comprises at lease one linear sliding receptacle and the second part comprises at least one linear sliding guide rail or vice versa, wherein the linear sliding receptacle and the linear sliding guide rails in conjunction form a linear sliding connector configured for establishing a releasable mechanical connection between the first part and the second part.

Embodiment 57: The medication device according to the preceding embodiment, wherein the linear sliding guide rails and the linear sliding receptacle are shaped complementary to each other.

Embodiment 58: The medication device according to any one of the preceding embodiments referring to a medication device, wherein the second part is flush with the first part.

Embodiment 59: A method for transcutaneously inserting a cannula into a body tissue, wherein the method comprises:
  a) providing a medication device according to any one of the preceding embodiments referring to a medication device;
  b) placing the first part onto the skin of the user;
  c) assembling the first part and the second part such that the first part and the second part establish at least one connection selected from the group consisting of: a form-fit connection, a press-fit connection; and
  d) triggering the integrated insertion mechanism, thereby driving the cannula from the storage position within the patch into the inserted position within the body tissue.

Embodiment 60: The method according to the preceding embodiment, wherein step b) is performed before conducting step c).

Embodiment 61: The method according to any one of the two preceding embodiments, wherein step b) is performed after conducting step c).

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
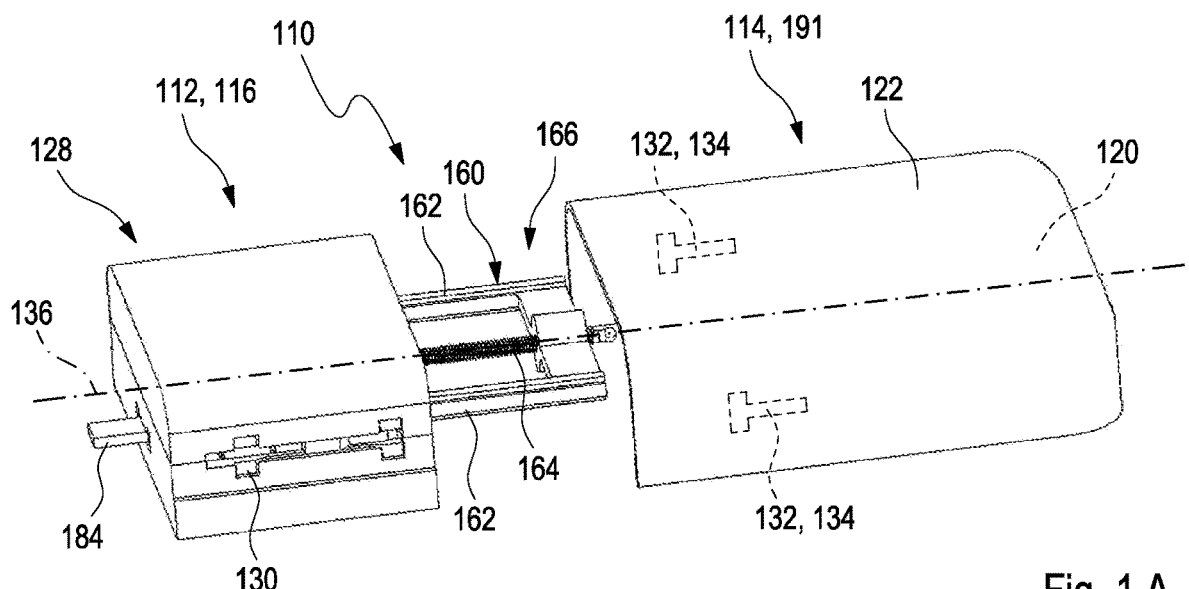
FIGS. 1A to 1C show an exemplary medication device in a disassembled view (FIGS. 1A-1B) and in an assembled view (FIG. 1C)
Figure 1:
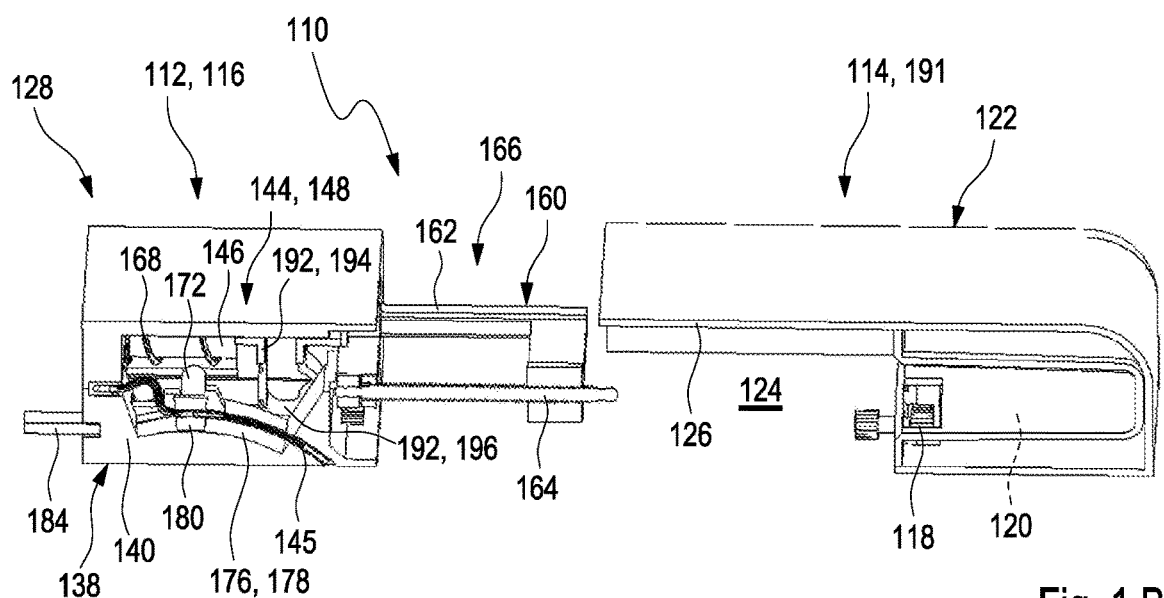
Figure 1:
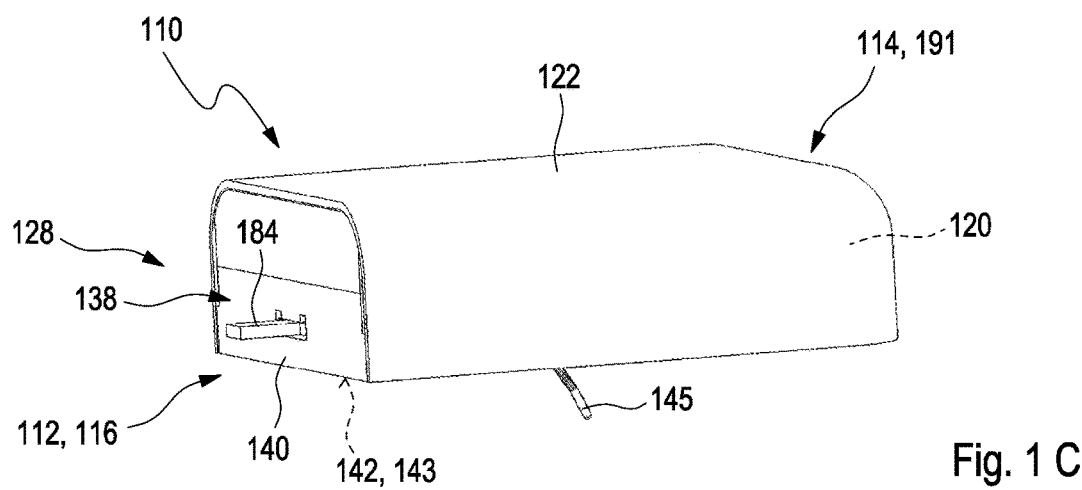

FIGS. 1A to 1C show an exemplary medication device 110 for delivering at least one therapeutical medical fluid to a user. In FIGS. 1A to 1B the medication device 110 is depicted in a disassembled state. A perspective view is shown in FIG. 1A whereas in FIG. 1B a sectional view is shown. In FIG. 1C, the medication device 110 in an assembled state is depicted. Thereby, the medication device 110 is shown in a sectional view.

The medication device 110 comprises at least one first part 112 and at least one second part 114. The first part 112 comprises at least one medical device 116 which will further be described below in more detail. The second part 114, as specifically depicted in FIG. 1B, comprises at least one medication pump 118. Further, the second part 114 comprises at least one electronics unit 120 and may comprise one or more energy storage devices (not shown), such as a battery.

The second part 114 may have a housing 122 configured for receiving the first part 112 at least partially. Thus, the housing 122, such as depicted in FIG. 1B may have a free volume 124. The free volume 124 may be configured for receiving the first part 112 such that the first part 112 is in direct contact with walls 126 of the second part 114.

The first part 112 and the second part 114 may be configured to establish at least one mechanical connection such as a form-fit connection. Specifically, the first part 112 and the second part 114 may be connectable via at least one linear sliding mechanism 128. The first part 112 may comprise at lease one linear sliding receptacle 130 and the second part 114 may comprise at least one linear sliding guide rail 132, such as depicted in FIG. 1A. The linear sliding receptacle 130 and the linear sliding guide rail 132 may be configured for establishing a releasable mechanical connection between the first part 112 and the second part 114. The linear sliding guide rail 132 may be formed as a protrusion 134 of the second part 114. The linear sliding guide rail 132 and the linear sliding receptacle 130 may be shaped complementary to each other. For example, the linear sliding receptacle 130 and the linear guide rail 132 may have an elongate shape and may extend along a longitudinal axis 136 of the first part 112 and/or of the second part 114.

Figure 2:
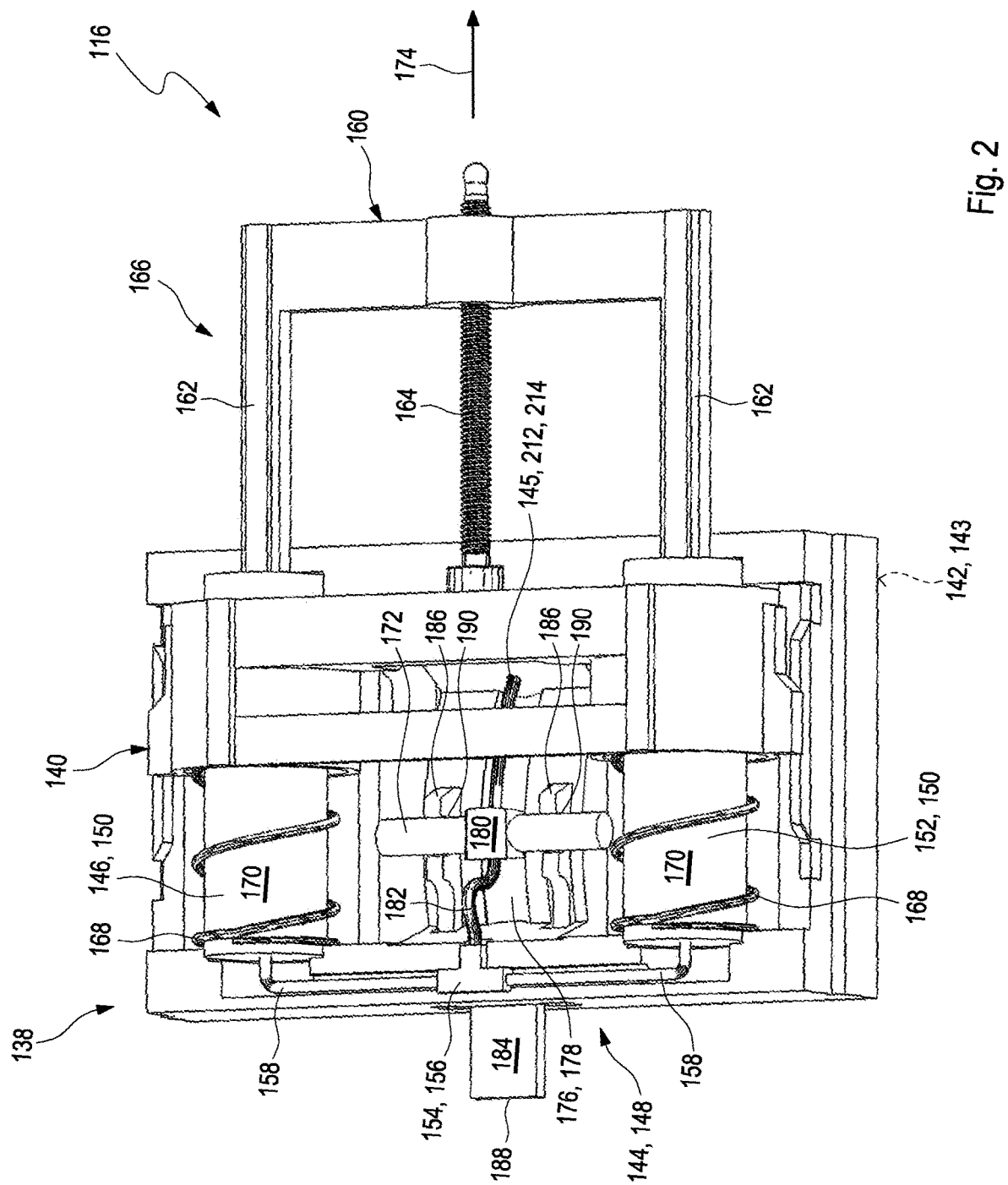
FIG. 2 shows an exemplary embodiment of a medical device according to this disclosure in a perspective view.
Figure 3:
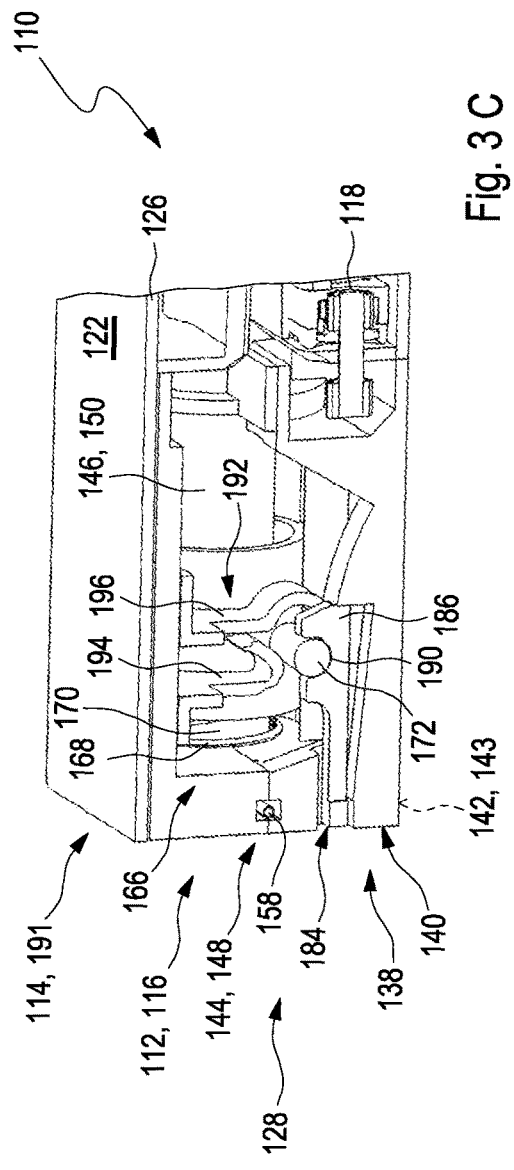
FIGS. 3A to 3G show exemplary embodiments of a medication device in different assembling states in various cross-sectional views (FIGS. 3B, 3D and 3F) and in various detailed views (FIGS. 3A, 3C, 3E, 3G)
Figure 3:
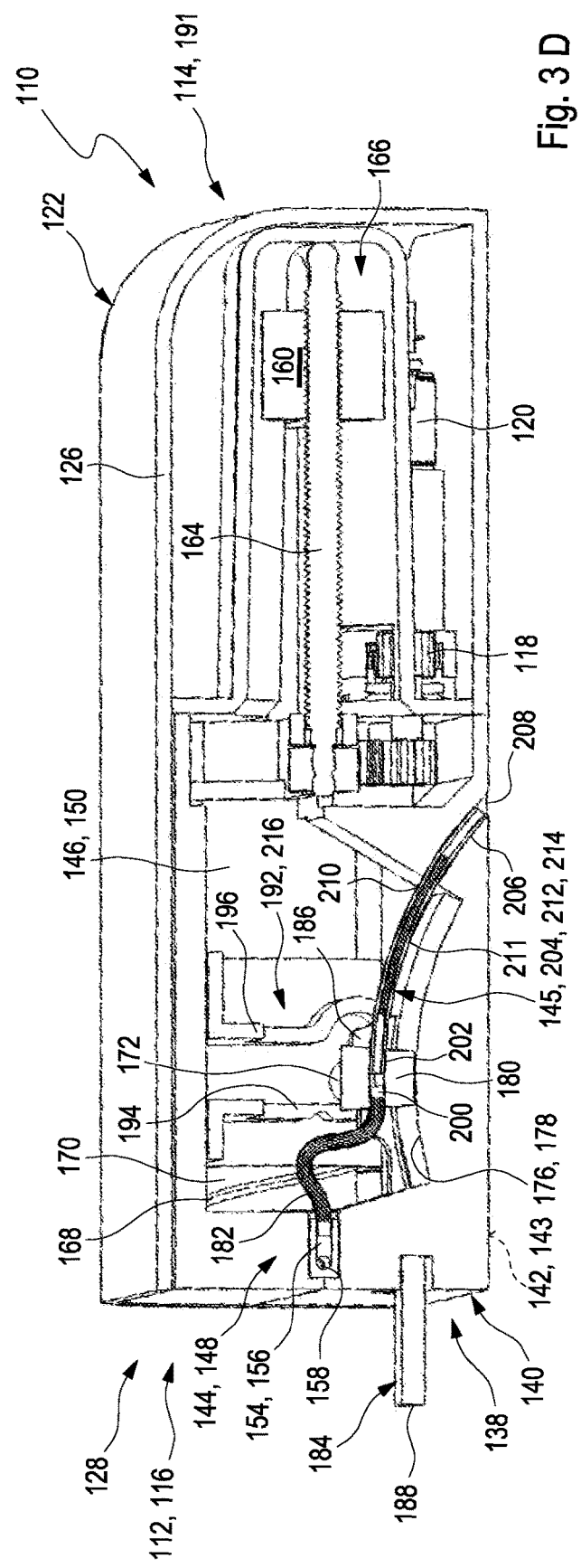
Figure 3:
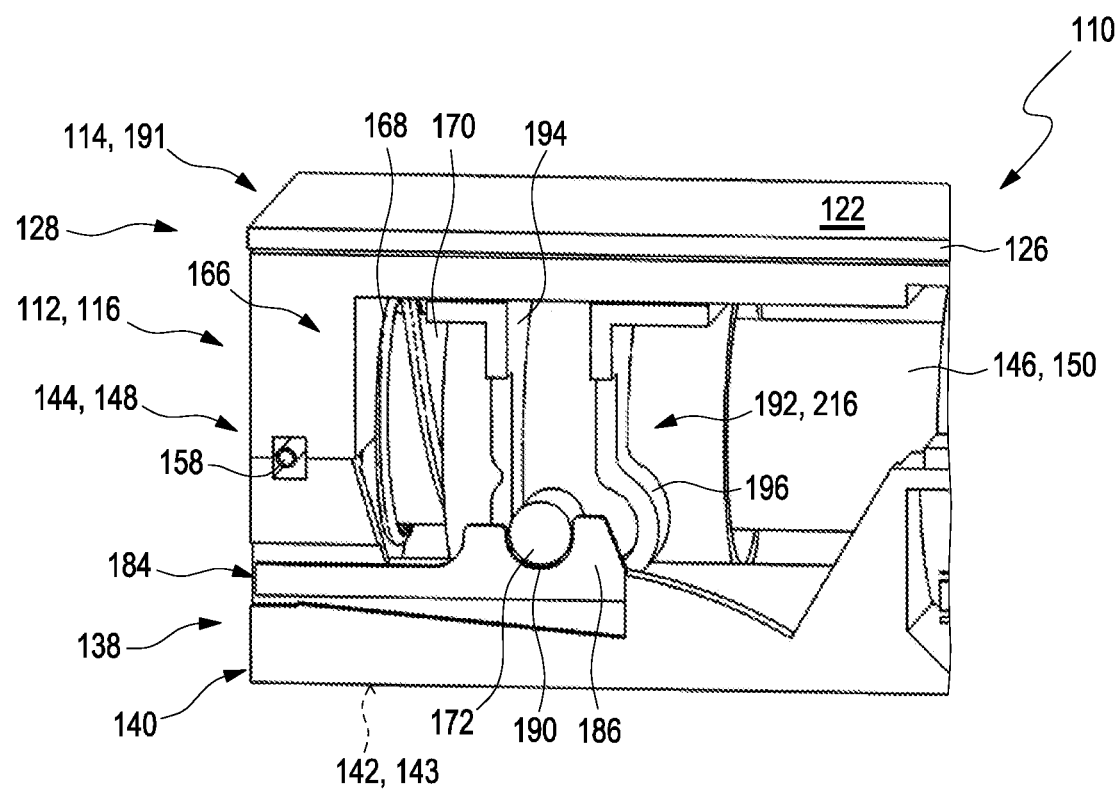
Figure 3:
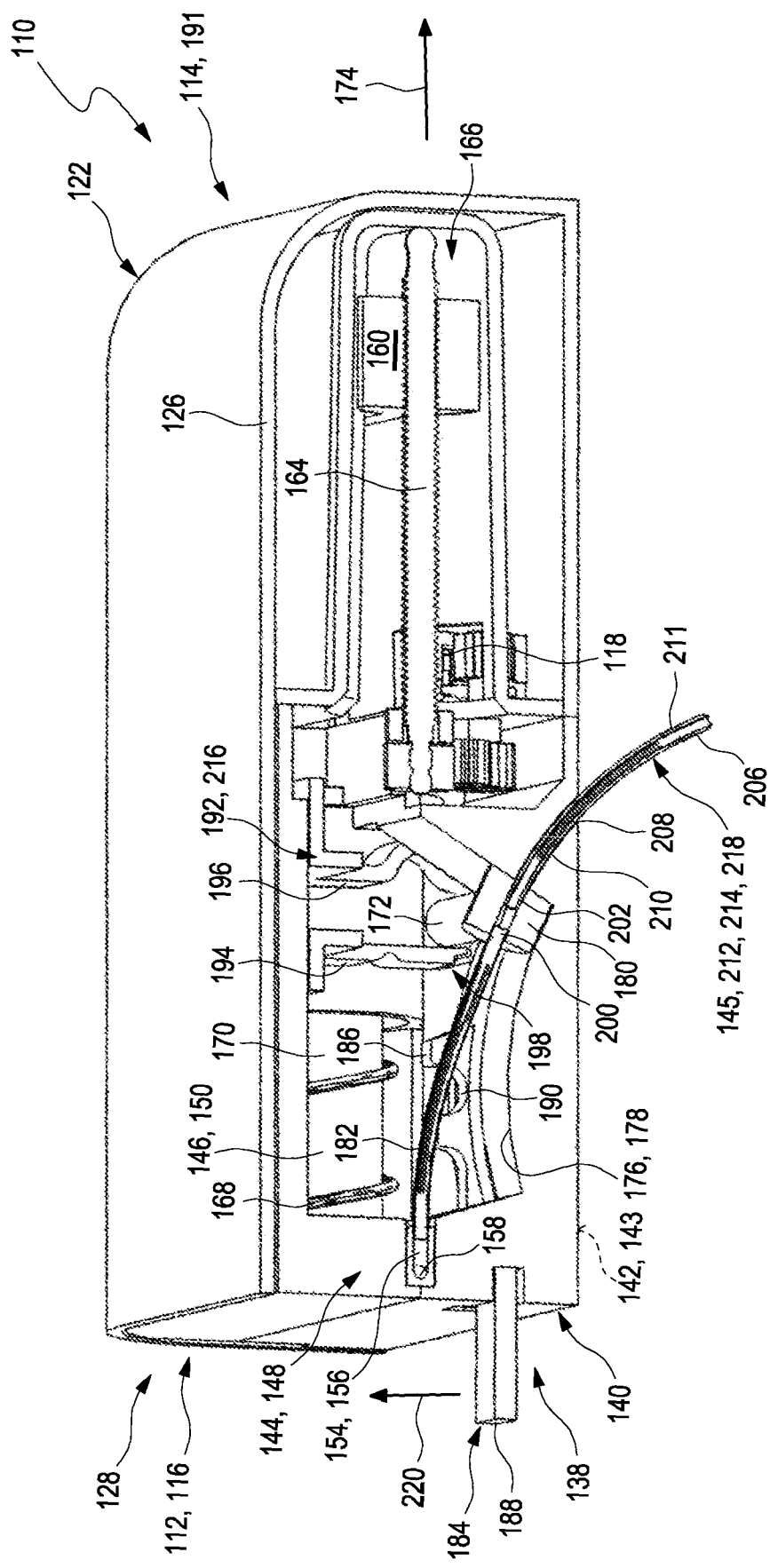
Figure 3:
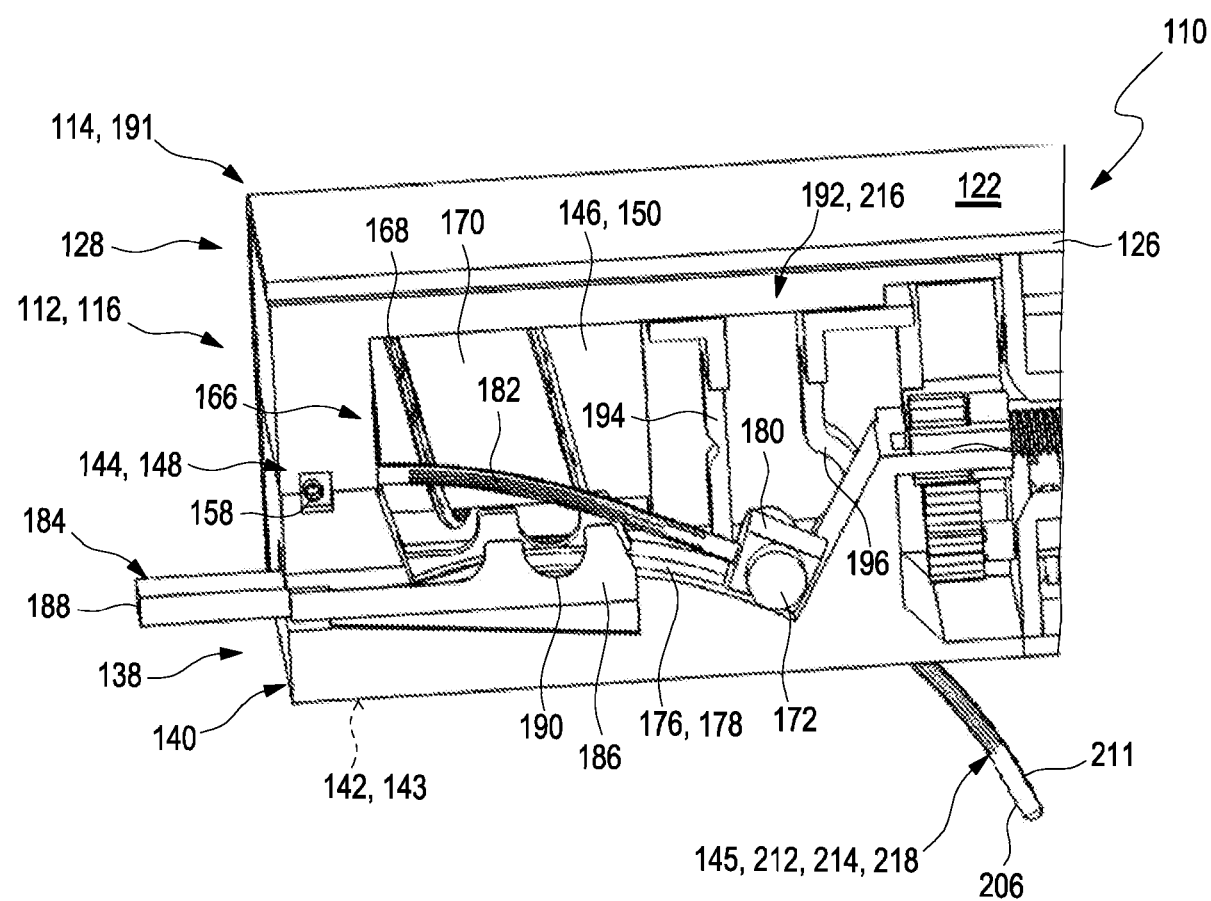

FIG. 2 shows an exemplary embodiment of a medical device 116 according to this disclosure in a perspective view. The medical device 116 may be a component of the first part 112 as depicted in FIGS. 1A to 1C. Thus, reference may be made to the description above.

The medical device 116 comprises at least one patch 138 configured to be mounted onto a skin of a user. The patch 138 comprises at least one patch base 140. Therefore, the patch 138, specifically the patch base 140, may comprise at least one adhesive surface 142. For example, the patch base 140 have a plaster 143 and the adhesive surface 142 may be part of the plaster 143. The patch 138 further comprises at least one integrated insertion mechanism 144 for driving a cannula 145 from a storage position within the patch 138 into an inserted position within the body tissue. The integrated insertion mechanism 144 is a spring driven insertion mechanism 148. The second part 114 as described above may be an external element 191 which is connectable to the medical device 116. The integrated insertion mechanism 144 may be configured to be driven by a force established when connecting the external element 191 to the medical device 116.

The patch 138 further comprises at least one reservoir 146 configured for storing at least one therapeutical medical fluid. Specifically, the reservoir 146 may be fillable with insulin. The reservoir 146 may comprise at least one cylindrical vial 150. The cylindrical vial 150 may specifically be rigid. The medical device 116 may further comprise at least one further reservoir 152. The further reservoir 152 and the reservoir 146 may be arranged next to each other. Thus, the reservoir 146 and the further reservoir 152 may be arranged in a space saving manner. The reservoir 146 and the further reservoir 152 may respectively be configured for storing the same therapeutical medical fluid. Thus, a supply of the therapeutical medical fluid may be increased and a number of exchanges of the reservoirs 146, 152 and thus of the medical device 116 may be reduced. However, alternatively, the further reservoir 152 may be configured for storing at least one further therapeutical medical fluid. Thereby, the medical device 116 may further comprise at least one mixing device 154. The mixing device 154 may comprise at least one static mixer 156 and may be configured for mixing the therapeutical medical fluid of the reservoir 146 and the further therapeutical medical fluid of the further reservoir 152 such that a mixture is formed before the fluids are applied. The reservoir 146 and the further reservoir 148 may respectively be fluidically connected to the mixing device 154 via tubes 158. The medical device 116 may further comprise at least one piston 160, specifically at least one piston rod 162. The piston 162 may be configured to displace the therapeutical medical fluid of the reservoirs 146, 152. The medical device 116 may further comprise at least one drive spindle 164. The drive spindle 164 may be operably connectable to the medication pump 118 as depicted in FIGS. 1A to 1B.

The integrated insertion mechanism 144 may further comprise at least one spring element 168. Specifically, the spring element 168 may be configured to be tensioned before insertion of the cannula 145 into the body tissue. The reservoir 146 may be at least partially received within an interior space 170 of the spring element 168. Thus, the reservoir 146 and the spring element 168 may be arranged in a space saving manner.

The integrated insertion mechanism 144 may further comprise at least one drive unit 166 configured for urging the cannula 145 in a direction of insertion, preferably by pushing the cannula 145. A functionality of the drive unit 166 may further be described below in more detail.

Moreover, the medical device 116 may further comprise at least one elongate element 172. The elongate element 172 may extend in a direction transverse, particularly perpendicular to a direction of extension of the spring element 168, as illustrated with arrow 174. The patch base 140 may comprise a sliding guide receptacle 176, preferably a linear sliding guide rail 178. The linear sliding guide rail 178 may extend parallel to a direction of extension of the cannula. The linear sliding guide rail 178 may be configured for receiving and guiding a protrusion 180 of the elongate element 172 at least partially. The protrusion 180 may be configured to slide within the linear sliding guide rail 178. The protrusion 180 may have a receptacle (not shown) for fixedly receiving one end of the cannula 145. Further, the reservoir 146 and the further reservoir 152 may be connectable to the cannula 145 via at least one fluid channel 182. In this embodiment, one end of the fluid channel 182 may be received in the protrusion 180 of the elongate element 172. The other end of the fluid channel 182 may be fluidically connected to the mixing device 154. Thus, the protrusion 180 may be configured to establish a fluid connection between the fluid channel 182, e.g., the reservoir 146 and the further reservoir 152, and the cannula 145. A functionality of the elongate element 172 may further be described below in more detail.

The integrated insertion mechanism 144 may further comprise at least one release button 184. The release button 184 may be an elongate element with a first end 186 and a second end 188. The first end 186 may have a receptacle 190. The receptacle 190 may have a shape which corresponds to a shape of the elongate element 172. For example, the elongate element 172 may be a cylinder having a round cross-section and the receptacle 190 may have a round shape correspondingly. The second end 188 of the release button 184 may be located outside of the patch 138. Thus, the second end 188 may be accessible for the user or the patient. A functionality of the release button 184 may further be described below in more detail.

FIGS. 3A to 3G show exemplary embodiments of the medication device 110 in different assembling states in various cross-sectional views (FIGS. 3B, 3D and 3F) and in various detailed views (FIGS. 3A, 3C, 3E, 3G). The medication device 110 may correspond at least partially to the medical device 110 according to FIGS. 1A and 1B. The medical device 116 of the medication device 110 may correspond at least partially to the medical device 116 according to FIG. 2. Thus, reference may be made to the description of FIGS. 1A to 2 above.

In FIG. 3A, a detailed view of the integrated insertion mechanism 144 is shown, before the first part 112 and the second part 114 are assembled. The medical device 116 may comprise the elongate element 172. The elongate element 172 is held in position by the release button 184 having the first end 186 and the second end 188 (not shown in FIG. 3A). The first end 186 may comprise the receptacle 190. Thus, the elongate element 172 may have a cylindrical shape and the receptacle 190 may have a corresponding round cross-section.

The integrated insertion mechanism 144 may further comprise at least one interlocking element 192 configured for securing the drive unit 166 in a fixed position. The interlocking element 192 may be fixedly connected to the drive unit 166. The interlocking element 192 may comprise at least one first interlocking element component 194 and at least one second interlocking element component 196. The first interlocking element component 194 and the second interlocking element component 196 may be at least partially made of an elastic material. The first interlocking element component 194 and the second interlocking element component196 may be configured to form a mechanical connection, specifically a form-fit connection as will further be described below in more detail. The interlocking element may have a snap closure 198 with a clip mechanism. The clicking mechanism may be a one-way clip mechanism.

In FIG. 3B, a cross-sectional view of the medication device 110 is shown. The medication device 10 comprises the first part 112 having the medical device 116. In FIG. 3B, the first part 112 and the second part 114 are partially assembled. At this stage, the first part 112 may already be placed and attached to a skin site of the user or the patient such as via the adhesive surface 142. Alternatively, the assembling of the first part 112 and the second part 114 may be conducted while the first part 112 is not yet attached to the skin site. As described above with regard to FIGS. 1A and 1B, the first part 112 and the second part 114 may be connectable via at least one linear sliding mechanism 128.

The elongate element 172 may comprise the protrusion 180. The reservoir 146 may be connectable to the cannula 145 via the fluid channel 182. One end 200 of the fluid channel 182 may be received in the protrusion 180 of the elongate element 172. One ex vivo end 202 of the cannula 145 may be received in the protrusion 180 as well. Thus, the protrusion 180 may be configured to establish a fluid connection between the fluid channel 182, e.g., the reservoir 146 and the further reservoir 152, and the cannula 145.

In FIG. 3B, the cannula 145 is depicted in a storage position 204. Thus, the cannula 145, specifically an in vivo end 206 of the cannula 145 may be received inside the patch 138. The patch 138 may have a passage opening 208 such that the cannula 145 may be able to be inserted into the body tissue as will further be described below in more detail. The patch 138 may further comprise at least one cannula receptacle 210 configured for receiving at least a section of the cannula 145. Moreover, the patch base 140 may comprise a sliding guide receptacle 176, preferably a linear sliding guide rail 178 which may be configured for receiving and guiding the protrusion 180 of the elongate element 172. Thus, the protrusion 180 may be configured to slide within the linear sliding guide rail 178.

The cannula 145 has a lumen which is fully or partially enclosed by a wall 211 of the cannula 145. Specifically, the cannula 145 may be a closed cannula with the wall 211. Further, the cannula 145 may be an infusion cannula 212. Specifically, the infusion cannula 212 may be at least partially made of steel, specifically stainless steel. The steel, specifically the stainless steel, may be biocompatible. Further, by applying the steel, specifically the stainless steel, a rigid infusion cannula may be provided. The cannula 145 may be a pre-bended cannula 214. Thus, the cannula 145, at least in absence of external forces, may be at least partially non-straight. Specifically, the cannula 145 may fully or partially be embodied as having the shape of a segment of a circle.

In the partially assembled state such as depicted in FIG. 3B, the interlocking element 192 may get in touch with the elongate element 172. Thus, a connection between the first interlocking element component 194 and at least one second interlocking element component 196 may be opened. The second interlocking element component 196 may enclose the elongate element 172. Meanwhile, the receptacle 190 of the release button 184 still secures the elongate element 172. This state is also depicted in FIG. 3C in a detailed view.

In FIG. 3D, a cross-sectional view of the medication device 110 is shown. The medication device 10 comprises the first part 112 having the medical device 116. In FIG. 3D, the first part 112 and the second part 114 are assembled. Thus, the housing 122 may be flush with the patch 138. The receptacle 190 of the release button 184 may still secure the elongate element 172. Thus, the receptacle 190 of the release button 184 may receive the elongate element 172. The elongate element 172 may be positioned between the first interlocking element component 194 and at least one second interlocking element component 196. Thus, the first interlocking element component 194 and at least one second interlocking element component 196 may enclose the elongate element 172. The first interlocking element component 194 and the second interlocking element component 196 may be configured to form a mechanical connection 216. This state is also depicted in FIG. 3E in a detailed view.

In FIG. 3F, a cross-sectional view of the medication device 110 is shown. The medication device 10 comprises the first part 112 having the medical device 116. In FIG. 3F, the first part 112 and the second part 114 are assembled and the integrated insertion mechanism 144 is triggered. Thus, the cannula 145 is in an inserted position 218.

The integrated insertion mechanism 144 may be triggerable via the release button 184. Thus, by pushing the second end 188 in a direction transverse to the skin site (not shown) as indicated with arrow 220, the first end 186, e.g., the receptacle 190 may release the elongate element 172. Thereby, the spring element 168 may relax in a direction of insertion such as indicated with arrow 174. Consequently, the drive unit 166 may move in the direction of insertion. As the interlocking element 194 may be fixedly connected to the drive unit 166, the elongate element 172 with the ex vivo end 202 of the cannula 145 being received in the protrusion 180 of the elongate element 172 also moves in the direction of insertion. The cannula 145, specifically the in vivo end 202 of the cannula 145 may extend through the passage opening 208 and may be inserted into the body tissue (not shown). Thereby, the fluid channel 182 which may be flexible may pass from a bended configuration to a stretched configuration. Thus, a fluid connection between the reservoir 146 and the cannula 145 via the fluid channel 182 may be maintained. This state is also depicted in FIG. 3G in a detailed view.

Figure 4:
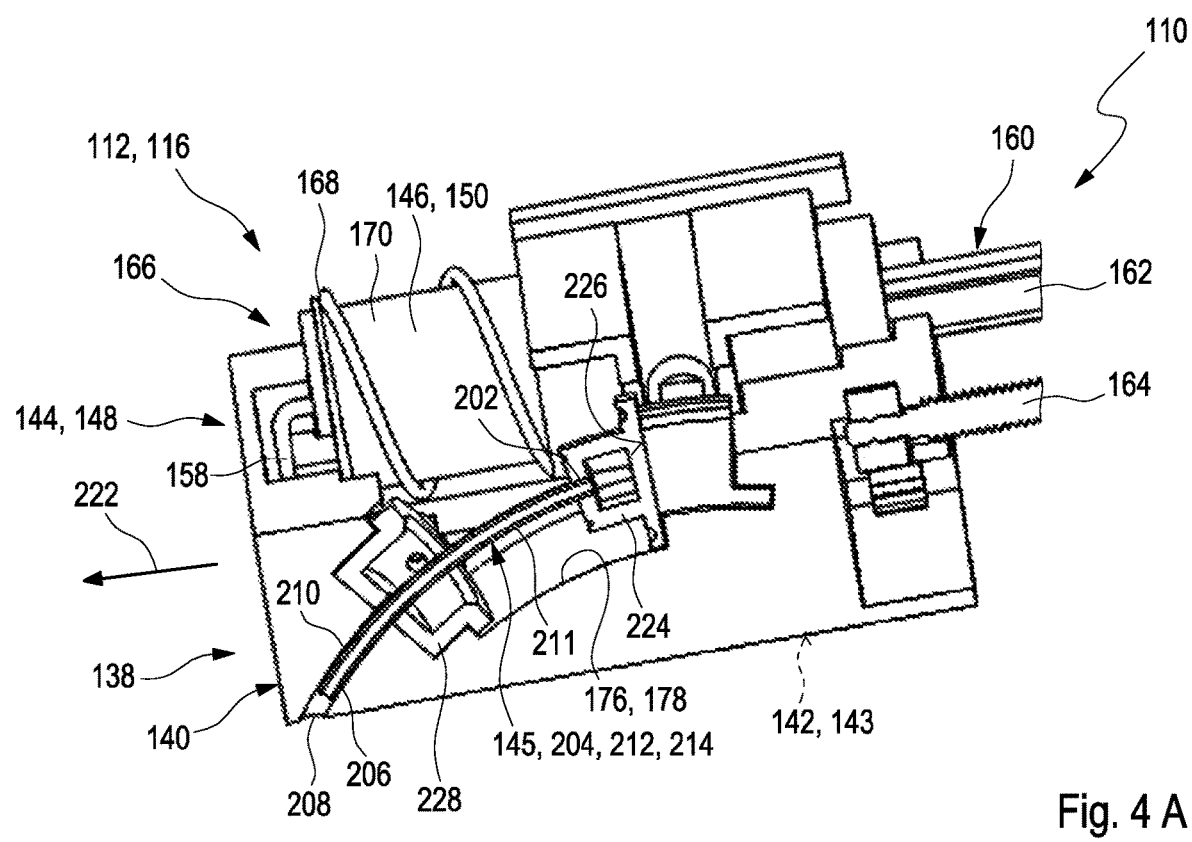
FIGS. 4A and 4B show an exemplary embodiment of a medical device in different cross-sectional views.
Figure 4:
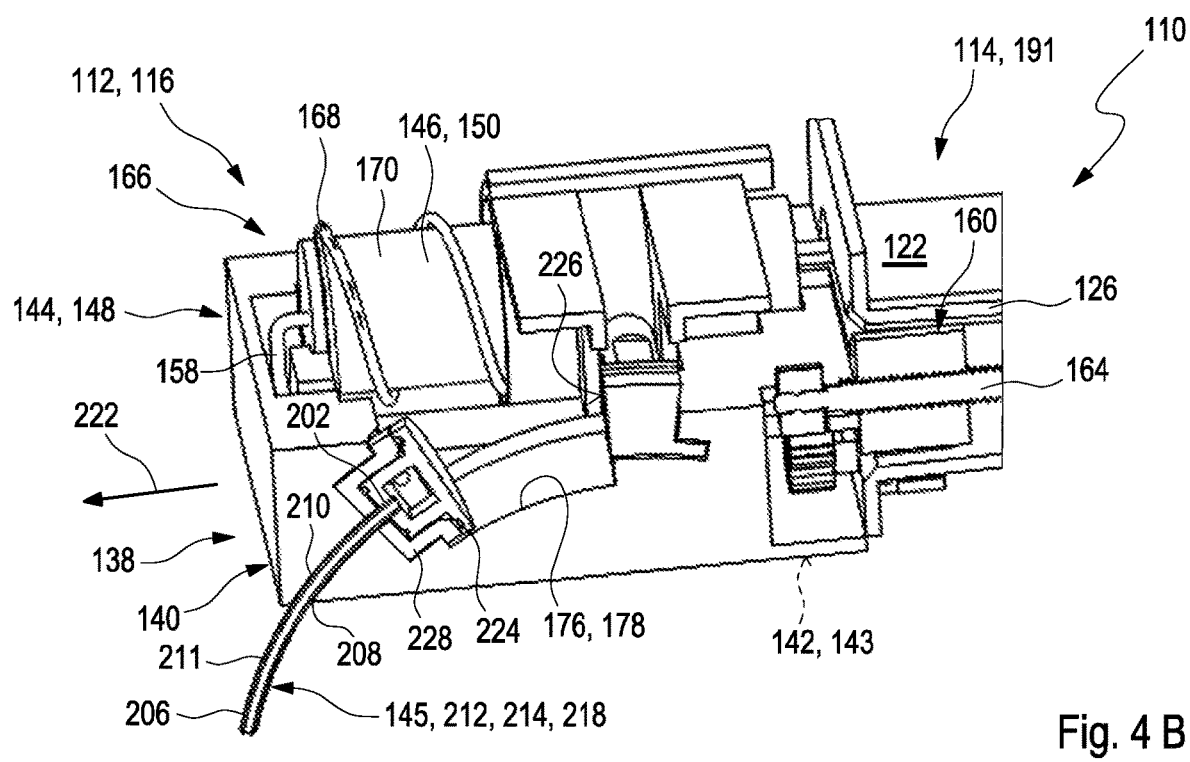

FIGS. 4A and 4B show an exemplary embodiment of a medical device 116 in different cross-sectional views. The medical device 116 partially corresponds to the medical device 116 as depicted in FIGS. 1A to 3G. Thus, reference may be made to the description above. The medical device 116 comprises the patch 138 and the cannula 145. Further, the patch 138 comprises the reservoir 146. For further details on these components, reference may be made to the description above.

The patch 138 also comprises the integrated insertion mechanism 144. Further, the medical device 116 may have the drive unit 166. In the medical device 116 according to FIGS. 4A and 4B the drive unit 166 may be moveable in a direction parallel to a direction of insertion as indicated by arrow 222. Thus, the spring element 168 may be compressible in the direction of insertion by the drive unit 166. The ex vivo end 202 of the cannula 145 may be fixedly attached to an element 224. The element 224 may be in direct contact with a support surface 226 of the drive unit 166.

In FIG. 4A, the cannula 145 is the storage position 204. Thus, the cannula 145, specifically the in vivo end 206 of the cannula 145 is received in the patch 138. By moving the drive unit 166 in the direction of insertion, the element 224 may slide along the sliding guide receptacle 176 of the path 138. Thus, the cannula 145 may be driven from the patch 138 into the inserted position 218 within the body tissue such as depicted in FIG. 4B. The element 224 may be received by a receptacle 228 which is arranged in proximity to the passage opening 208. Specifically, the element 224 may be configured to seal the receptacle 228.

Further, by moving the drive unit 166 in the direction of insertion, the spring element 168 may be tensioned. Thus, in the inserted position 218, the drive unit 166 may be put back by the tension force of the spring element 168, while the element 224 stays within the receptacle 228.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 medication device
112 first part
114 second part
116 medical device
118 medication pump
120 electronics unit
122 housing
124 free volume
126 wall
128 linear sliding mechanism
130 linear sliding receptacle
132 linear sliding guide rail
134 protrusion
136 longitudinal axis
138 patch
140 patch base
142 adhesive surface
143 plaster
144 integrated insertion mechanism
145 cannula
146 reservoir
148 spring driven insertion mechanism
150 cylindrical vial
152 further reservoir
154 mixing device
156 static mixer
158 tube
160 piston
162 piston rod
164 drive spindle
166 drive unit
168 spring element
170 interior space
172 elongate element
174 arrow
176 sliding guide receptacle
178 linear sliding guide rail
180 protrusion
182 fluid channel
184 release button
186 first end
188 second end
190 receptacle
191 external element
192 interlocking element
194 first interlocking element receptacle
196 second interlocking element receptacle
198 snap closure
200 end
202 ex vivo end
204 storage position
206 in vivo end
208 passage opening
210 cannula receptacle
211 wall
212 infusion cannula
214 pre-bended cannula
216 mechanical connection
218 inserted position
220 arrow
222 arrow
224 element
226 support surface
228 receptacle

What is claimed is:

1. A medical device for transcutaneously inserting a cannula into body tissue, comprising:
a cannula having a wall that at least partially encloses a lumen;
a patch configured for mounting onto skin of a user, the patch comprising a base and a reservoir configured for storing a medical fluid;
the patch further comprising a spring driven inserter, the inserter further comprising:

a drive configured for urging the cannula in an insertion direction from a storage position within the patch to an inserted position within the body tissue;

at least one interlocking component configured for securing the drive in a fixed position, the at least one interlocking component being fixedly connected to the drive; and an elongate element wherein the cannula is fixedly received in the elongate element and the at least one interlocking component is configured to enclose the elongate element.

2. The medical device according to claim 1, wherein the cannula is selected from the group consisting of an insertion cannula for inserting an infusion cannula into the body tissue and an infusion cannula.

3. The medical device according to claim 1, wherein the inserter comprises a sliding inserter.

4. The medical device according to claim 1, wherein the medical device is connectable to at least one external element, wherein the inserter is configured to be driven by a force established when connecting the external element to the medical device.

5. The medical device according to claim 1, wherein the inserter further comprises a spring that is tensible parallel to the insertion direction and the drive is configured to compress the spring.

6. The medical device according to claim 1, wherein the at least one interlocking component comprises first and second components at least partially made of an elastic material, wherein the first and second components are configured to form a mechanical connection.

7. The medical device according to claim 6, wherein the elongate element has a protrusion, wherein the cannula is fixedly received within a receptacle of the protrusion.

8. The medical device according to claim 7, wherein the inserter further comprises a release button configured for holding the elongate element in a predetermined position and for subsequently releasing the elongate element.

9. The medical device according to claim 7, wherein the base comprises a sliding guide receptacle configured for at least partially receiving the protrusion and the protrusion is configured to slide within the sliding guide receptacle.

10. A medication device for delivering at least one medical fluid to a user, comprising:
a medical device in accordance with claim 1; and
a medication pump fluidly connectable to the cannula, the medication pump having electronics.

11. The medication device according to claim 10, wherein the pump is a reusable component.

12. The medication device according to claim 10, wherein the medical device and the pump are connectable by a form-fit connection or a press-fit connection.

13. A method for transcutaneously inserting a cannula into a body tissue, comprising:
a) providing a medical device in accordance with claim 1;
b) providing a medication pump fluidly connectable to the cannula, the medication pump having electronics;
c) placing the medical device onto the skin of the user;
d) assembling the medical device and the pump such that the medical device and the pump establish a form-fit or a press-fit connection; and
e) triggering the inserter and thereby driving the cannula from the storage position within the patch to the inserted position within the body tissue.

14. The medical device according to claim 1 wherein the at least one interlocking component comprises a snap closure.

15. A medical device for transcutaneously inserting a cannula into body tissue, comprising:
a cannula having a wall that at least partially encloses a lumen;
a patch configured for mounting onto skin of a user, the patch comprising a base and a reservoir configured for storing a medical fluid;
the patch further comprising a spring driven inserter, the inserter further comprising:
a drive configured for urging the cannula in an insertion direction from a storage position within the patch to an inserted position within the body tissue;
an elongate element wherein the cannula is fixedly received in the elongate element;
at least one interlocking component configured for securing the drive in a fixed position relative to the elongate element, the at least one interlocking component being fixedly connected to the drive; and
a release element directly engageable with the elongate element to secure the drive in a first position with the cannula in the storage position and selectively releasable from the elongate element to allow the drive to move from the first position and thereby drive the cannula in the insertion direction.

16. The medical device according to claim 15, wherein the release element is engageable with the elongate element on opposite sides of the cannula.

17. The medical device according to claim 16, wherein the drive comprises a pair of springs for urging the cannula in the insertion direction and the release element is disposed between the pair of springs.

18. The medical device according to claim 15, wherein the elongate element has a protrusion and the cannula is fixedly received within a receptacle of the protrusion and the base comprises a sliding guide receptacle configured for at least partially receiving the protrusion and the protrusion is configured to slide within the sliding guide receptacle; and
wherein the release element is engageable with the elongate member on opposite sides of the protrusion.

19. The medical device according to claim 15 wherein the release element is an elongate release element having a first end which defines a receptacle for receiving the elongate element and a second end which projects from the patch, the second end being moveable by a user to thereby release the elongate element from the elongate release element.

* * * * *